US008221968B2

(12) United States Patent
Becker et al.

(10) Patent No.: US 8,221,968 B2
(45) Date of Patent: Jul. 17, 2012

(54) APPARATUS, METHOD AND SYSTEM FOR CREATING, HANDLING, COLLECTING AND INDEXING SEED AND SEED PORTIONS FROM PLANT SEED

(75) Inventors: Steven Michael Becker, Johnston, IA (US); Jason Cope, Ankeny, IA (US); David Kurth, Grimes, IA (US); Joshua L Mongan, St. Charles, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 13/313,426

(22) Filed: Dec. 7, 2011

(65) Prior Publication Data

US 2012/0073416 A1 Mar. 29, 2012

Related U.S. Application Data

(62) Division of application No. 12/336,084, filed on Dec. 16, 2008.

(60) Provisional application No. 61/014,366, filed on Dec. 17, 2007.

(51) Int. Cl.
*C12Q 1/10* (2006.01)

(52) U.S. Cl. ......................................................... 435/4

(58) Field of Classification Search ...... 435/4; 356/318; 47/58.1 SE, 58.1
See application file for complete search history.

(56) References Cited

U.S. PATENT DOCUMENTS

| | | |
|---|---|---|
| 2,675,942 A | 4/1954 | Vogelsang |
| 2,875,942 A | 3/1959 | Wilson |
| 3,344,769 A | 10/1967 | Williams |
| 3,460,492 A | 8/1969 | Dickinson, III et al. |
| 3,636,486 A | 1/1972 | Ioffe et al. |
| 3,741,793 A | 6/1973 | Simmons |
| 3,830,902 A | 8/1974 | Barnes |
| 3,831,736 A | 8/1974 | Barnes |
| 3,884,347 A | 5/1975 | Gallagher et al. |

(Continued)

FOREIGN PATENT DOCUMENTS

DE 196 16 216 A1 10/1997

(Continued)

OTHER PUBLICATIONS

International Search Report for International Appl. No. PCT/US2007/084583, mailed Feb. 10, 2008.

(Continued)

*Primary Examiner* — Kent L Bell
(74) *Attorney, Agent, or Firm* — Alston & Bird LLP

(57) ABSTRACT

An apparatuses, methods and systems for creating, handling and collecting seed portions are highly beneficial. The apparatus includes a carrier having one or more carrying positions adapted to carry a seed. The carrying positions having a seed orienter adapted to orient the seed relative to the carrying position in the carrier for creating seed portions therefrom. The method includes taking a carrier having one or more carrying positions, orienting a seed relative to the carrying position in the carrier, ablating the seed with a seed ablation device, and communicating seed portions through a manifold into a compartment layer. The system includes a seed manifold adapted to dock thereon a seed carrier having pre-positioned and pre-oriented seed therein. Seed and seed portions removed from the seed in the carrier are communicated into a collector and compartment layer respectively using the seed manifold.

20 Claims, 29 Drawing Sheets

U.S. PATENT DOCUMENTS

| | | | |
|---|---|---|---|
| 3,921,459 A | 11/1975 | Willett | |
| 3,930,212 A | 12/1975 | Ioffe et al. | |
| 3,991,704 A | 11/1976 | Hulstein et al. | |
| 4,238,658 A | 12/1980 | Kalnin et al. | |
| 4,278,625 A | 7/1981 | Dedolph | |
| 4,300,462 A | 11/1981 | Wilkins et al. | |
| 4,301,762 A | 11/1981 | Burnett, Jr. | |
| 4,413,014 A | 11/1983 | Melancon | |
| 4,436,207 A | 3/1984 | Klukis | |
| 5,097,625 A | 3/1992 | Kaneko et al. | |
| 5,238,121 A | 8/1993 | Frisbie | |
| 6,299,368 B1 | 10/2001 | Tavularis | |
| 6,409,007 B1 | 6/2002 | Malon | |
| 6,659,338 B1 | 12/2003 | Dittmann et al. | |
| 6,705,827 B2 | 3/2004 | Keller et al. | |
| 7,024,817 B2 | 4/2006 | Zehner et al. | |
| 7,043,070 B2 | 5/2006 | Vilella | |
| 7,197,374 B2 | 3/2007 | Silverbrook et al. | |
| 7,207,485 B2 | 4/2007 | Silverbrook et al. | |
| 7,502,113 B2 | 3/2009 | Deppermann et al. | |
| 7,591,101 B2 | 9/2009 | Deppermann | |
| 7,600,642 B2 | 10/2009 | Deppermann | |
| 7,611,842 B2 | 11/2009 | Deppermann et al. | |
| 7,685,768 B2 | 3/2010 | Deppermann | |
| 7,703,238 B2 | 4/2010 | Deppermann et al. | |
| 7,735,626 B2 | 6/2010 | Cope et al. | |
| 7,767,883 B2 | 8/2010 | Deppermann et al. | |
| 7,849,632 B2 | 12/2010 | Deppermann et al. | |
| 7,877,926 B2 | 2/2011 | Deppermann | |
| 7,915,006 B2 | 3/2011 | Cope et al. | |
| 7,941,969 B2 | 5/2011 | Deppermann et al. | |
| 7,968,282 B2 * | 6/2011 | Cope | 435/4 |
| 7,998,669 B2 | 8/2011 | Deppermann et al. | |
| 7,998,699 B2 | 8/2011 | Deppermann et al. | |
| 8,028,469 B2 | 10/2011 | Deppermann et al. | |
| 8,031,910 B2 | 10/2011 | Jones et al. | |
| 2003/0070567 A1 | 4/2003 | Thomas | |
| 2005/0210744 A1 | 9/2005 | Watanabe | |
| 2006/0042527 A1 | 3/2006 | Deppermann | |
| 2006/0046244 A1 | 3/2006 | Deppermann | |
| 2006/0046264 A1 | 3/2006 | Deppermann et al. | |
| 2006/0048247 A1 | 3/2006 | Deppermann | |
| 2006/0048248 A1 | 3/2006 | Deppermann | |
| 2006/0222958 A1 | 10/2006 | Yamaguchi et al. | |
| 2007/0204366 A1 | 8/2007 | Deppermann et al. | |
| 2007/0207485 A1 | 9/2007 | Deppermann et al. | |
| 2008/0131254 A1 | 6/2008 | Cope et al. | |
| 2008/0131924 A1 | 6/2008 | Cope et al. | |
| 2008/0317279 A1 | 12/2008 | Deppermann et al. | |
| 2009/0061449 A1 | 3/2009 | Chung et al. | |
| 2009/0155878 A1 | 6/2009 | Becker et al. | |
| 2009/0215060 A1 | 8/2009 | Deppermann et al. | |
| 2010/0044356 A1 | 2/2010 | Cope | |
| 2010/0086963 A1 | 4/2010 | Deppermann et al. | |
| 2010/0209228 A1 | 8/2010 | Cope et al. | |
| 2010/0209576 A1 | 8/2010 | Cope et al. | |
| 2010/0299790 A1 | 11/2010 | Deppermann et al. | |
| 2011/0081716 A1 | 4/2011 | Deppermann | |
| 2011/0117570 A1 | 5/2011 | Cope et al. | |
| 2011/0160068 A1 | 6/2011 | Becker et al. | |
| 2011/0217700 A1 | 9/2011 | Deppermann et al. | |
| 2011/0225680 A1 | 9/2011 | Cope | |

FOREIGN PATENT DOCUMENTS

| | | |
|---|---|---|
| EP | 0 611 604 A2 | 8/1994 |
| EP | 1 126 268 A1 | 8/2001 |
| GB | 2 293 744 A1 | 4/1996 |
| WO | WO 80/01531 A1 | 8/1980 |
| WO | WO 03/100381 A1 | 12/2003 |
| WO | WO 2007/103769 A3 | 9/2007 |
| WO | WO-2007/103786 A2 | 9/2007 |
| WO | WO-2008/150798 A1 | 12/2008 |

OTHER PUBLICATIONS

International Search Report for International Appl. No. PCT/US2008/086992, mailed Jul. 9, 2009.

International Search Report and Written Opinion for International Appl. No. PCT/US2009/054644, mailed Feb. 3, 2010.

John W. K. Leung and K . K. Lai; Performance analysis of automatic assembly systems with in-line parallel stations; IMA Journal of Mathematics Applied in Business & Industry; 1997; pp. 1-22; vol. 8, No. 1.

Krone, Todd L., "Genetic Analysis and Breeding for Kernel Methionine Content in Maize (*Zea mays* L.)", Thesis submitted in partial fulfillment of requirements for the degree of Doctor of Philisophy, University of Minnesota (Aug. 1994).

Sangtong V., et al., "Serial Extraction of Endosperm Drillings (SEED)—A Method for Detecting Transgenes and Proteins in Single Viable Maize Kernels", Plant Molecular Biology Reporter 19:151-158 (Jun. 2001).

\* cited by examiner

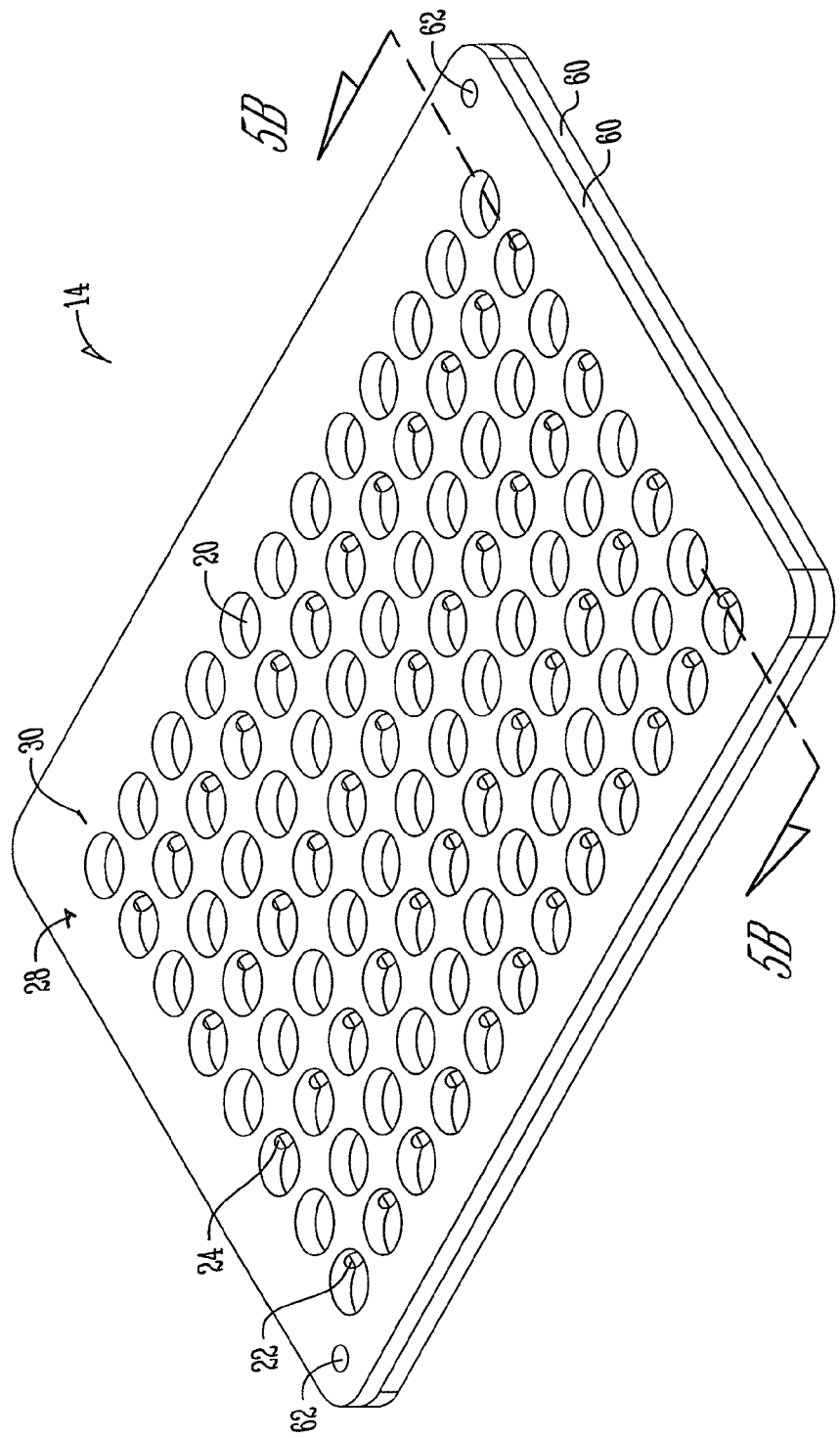

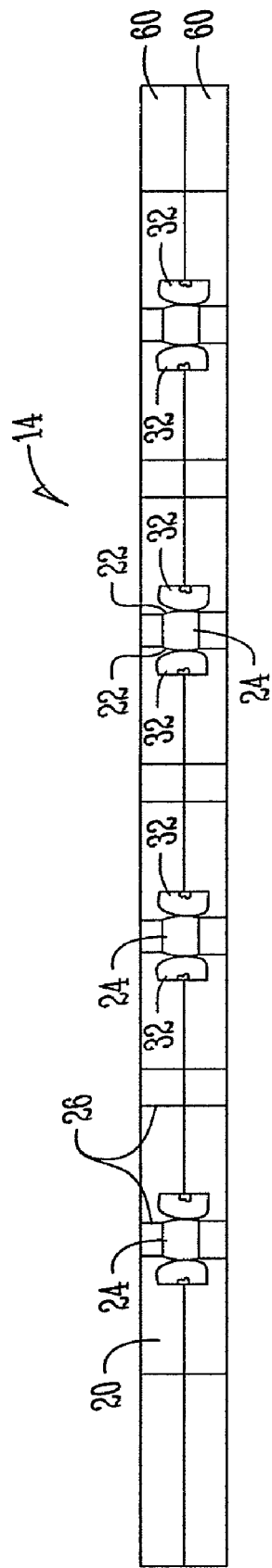

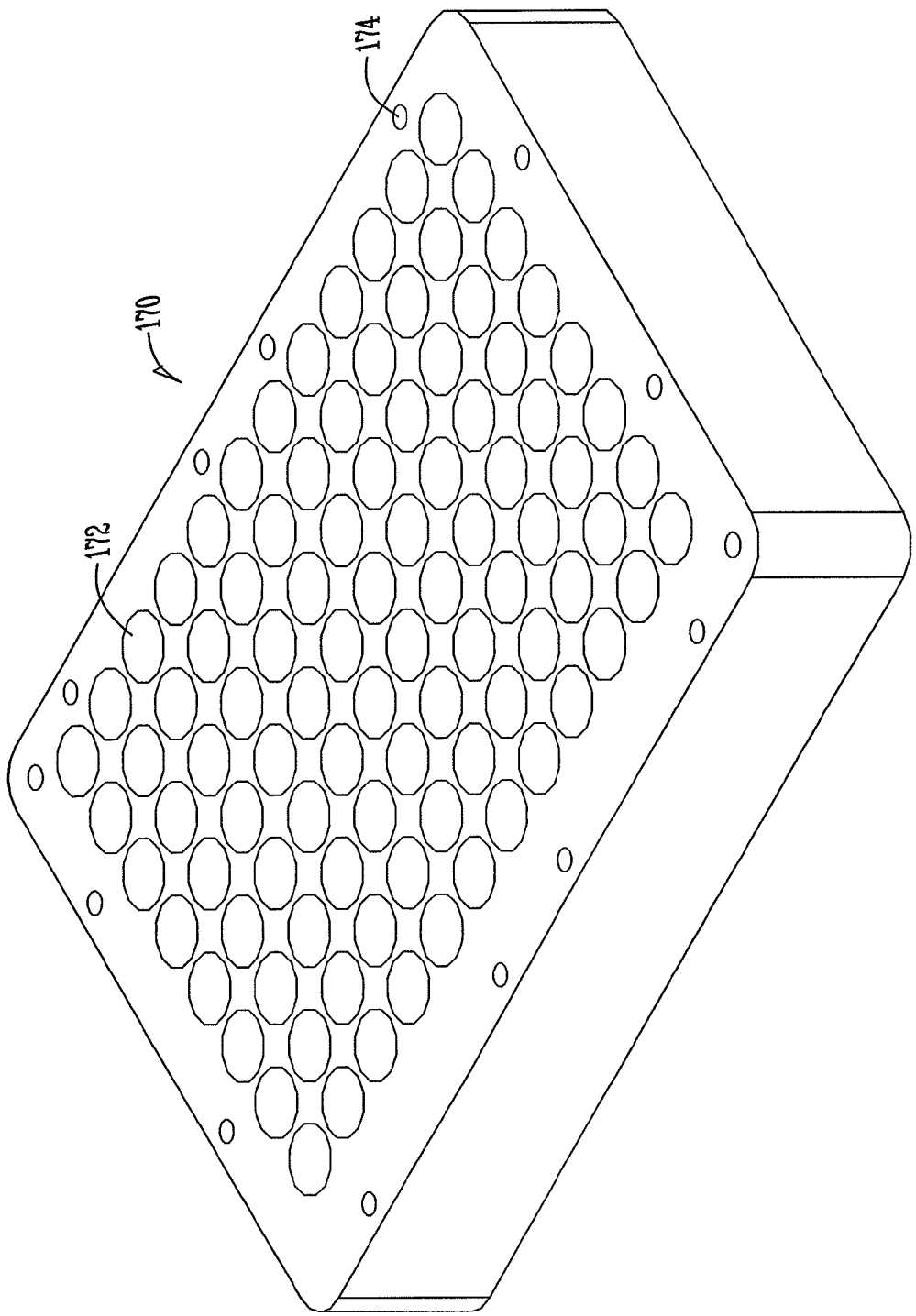

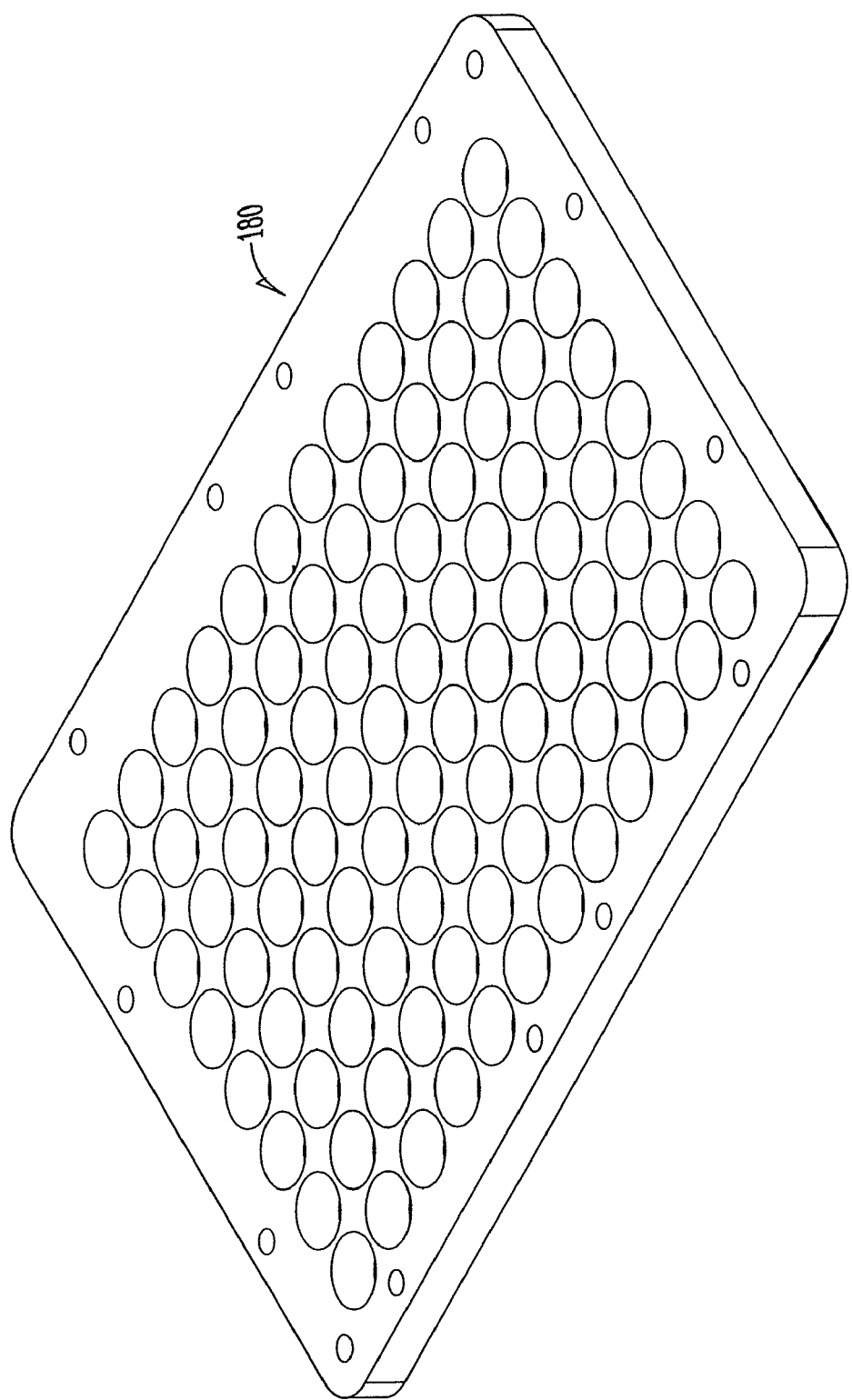

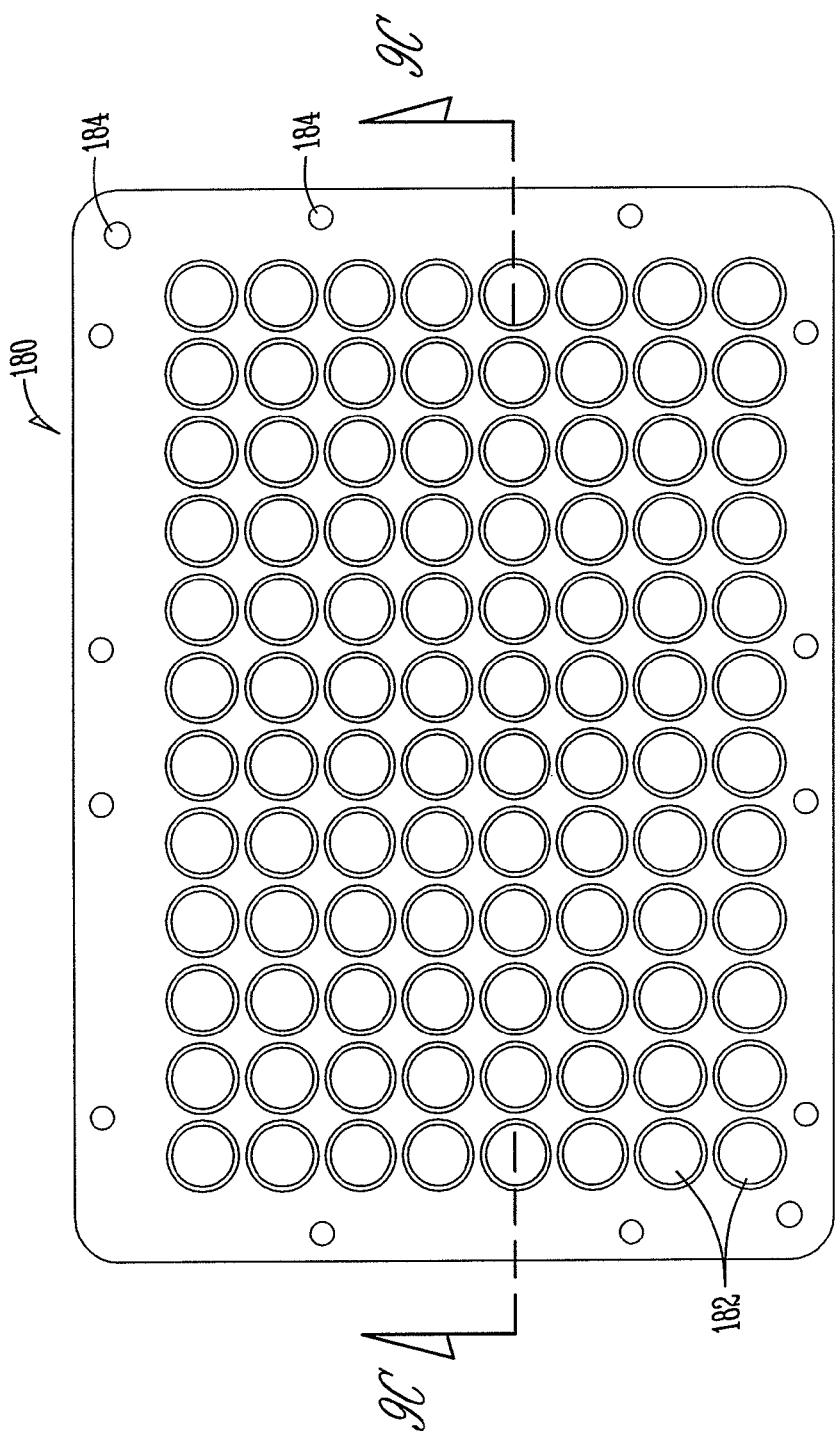
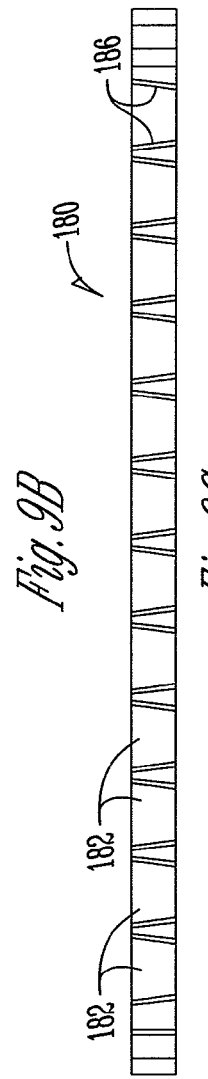
Fig. 9B
Fig. 9C

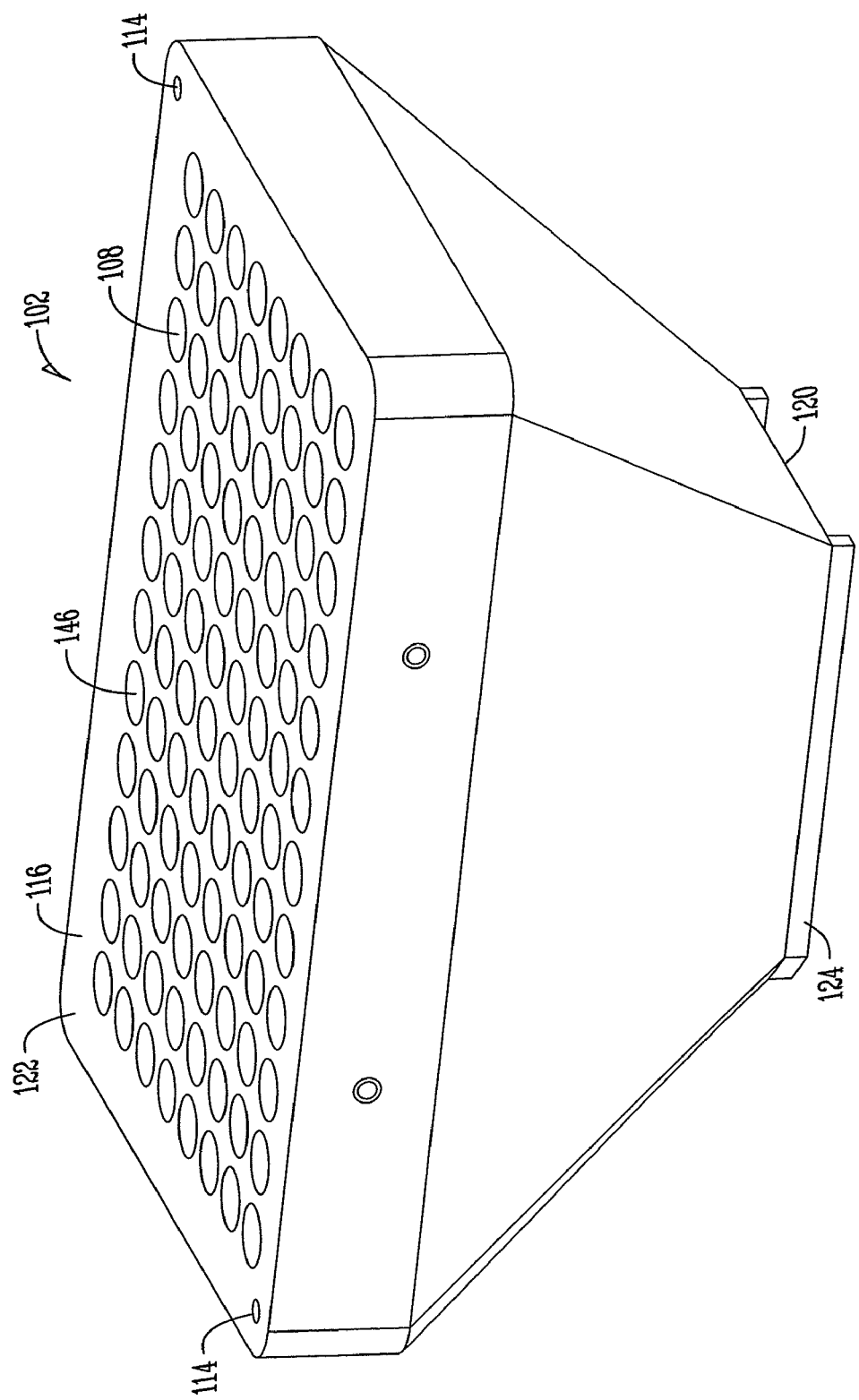

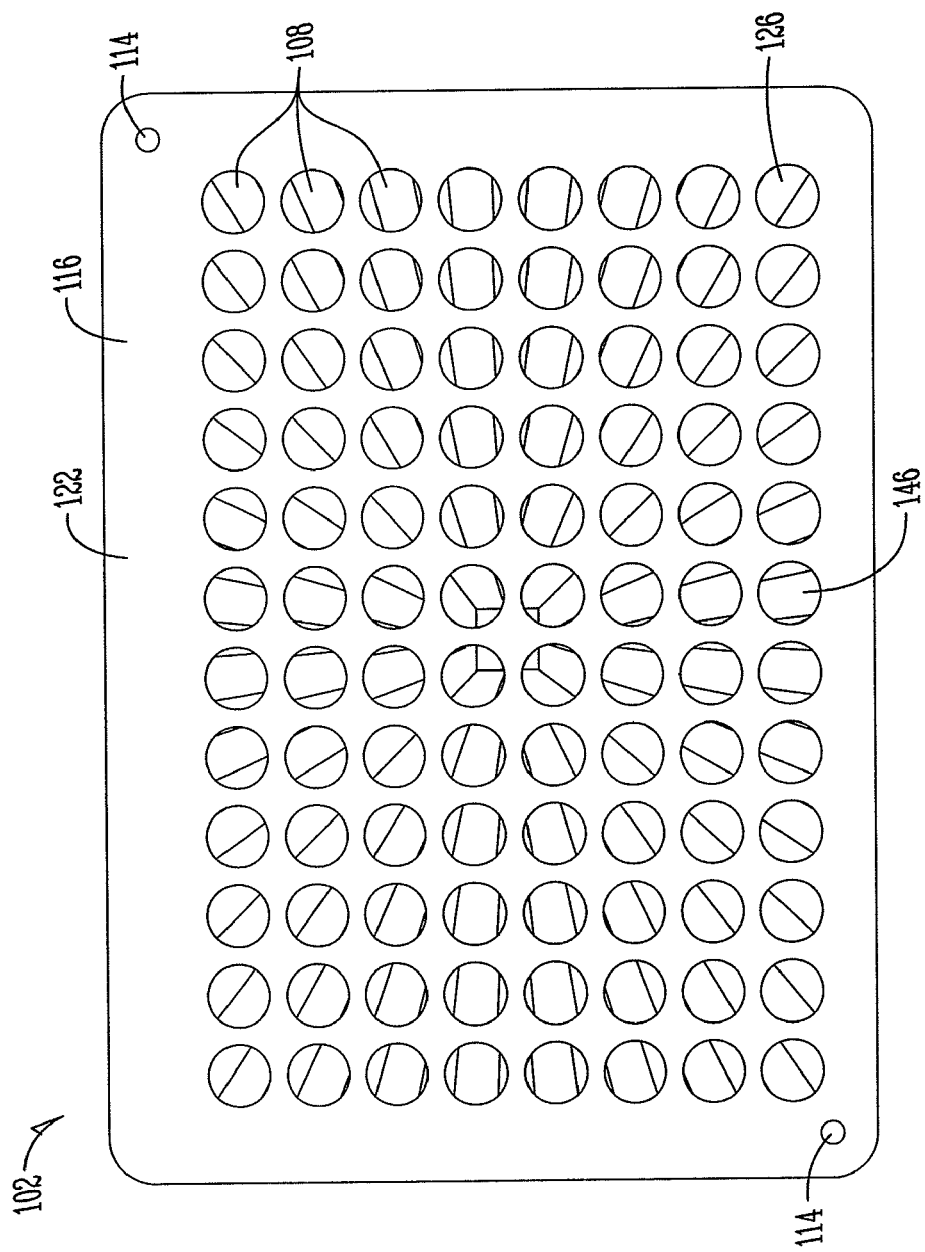

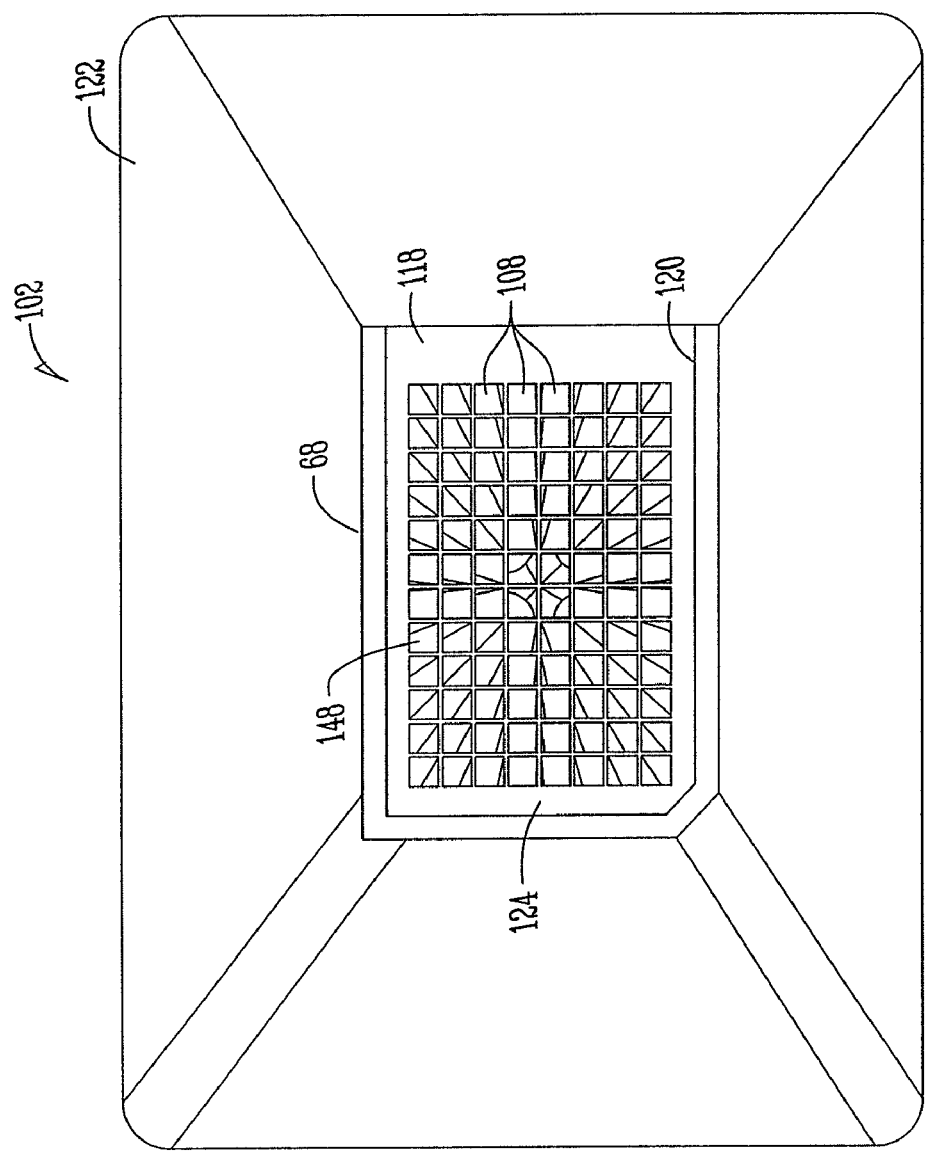

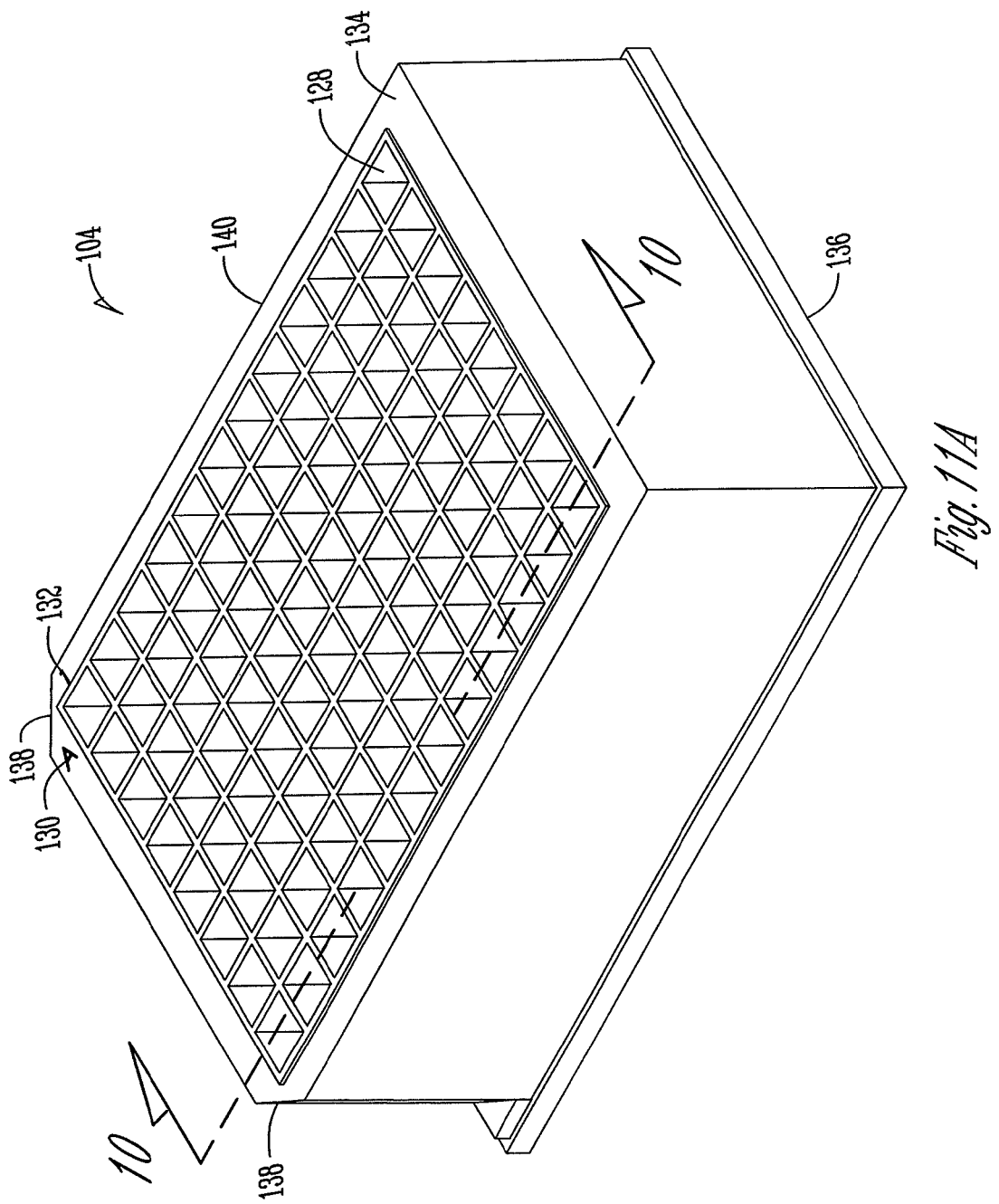

APPARATUS, METHOD AND SYSTEM FOR CREATING, HANDLING, COLLECTING AND INDEXING SEED AND SEED PORTIONS FROM PLANT SEED

CROSS-REFERENCE TO RELATED APPLICATIONS

This application is a divisional application of U.S. patent application Ser. No. 12/336,084, filed Dec. 16, 2008, which claims priority under 35 U.S.C. §119 of a provisional application Ser. No. 61/014,366 filed Dec. 17, 2007, each of which is hereby incorporated by reference in its entirety.

FIELD OF THE INVENTION

The present invention relates generally to an apparatus, method and system for creating, collecting and indexing seed portions from individual seed in an efficient way.

BACKGROUND OF THE INVENTION

It is conventional practice in plant breeding or plant advancement experiments to grow plants from seed of known parentage. The seed are planted in experimental plots, growth chambers, greenhouses, or other growing conditions in which they are either cross pollinated with other plants of known parentage or self pollinated. The resulting seed are the offspring of the two parent plants or the self pollinated plant, and are harvested, processed and planted to continue the plant breeding cycle. Specific laboratory or field-based tests may be performed on the plants, plant tissues, seed or seed tissues, in order to aid in the breeding or advancement selection process.

Generations of plants based on known crosses or self pollinations are planted and then tested to see if these lines or varieties are moving towards characteristics that are desirable in the marketplace. Examples of desirable traits include, but are not limited to, increased yield, increased homozygosity, improved or newly conferred resistance and/or tolerance to specific herbicides and/or pests and pathogens, increased oil content, altered starch content, nutraceutical composition, drought tolerance, and specific morphological based trait enhancements.

As can be appreciated and as is well known in the art, these experiments can be massive in scale. They involve a huge labor force ranging from scientists to field staff to design, plant, maintain, and conduct the experiments, which can involve thousands or tens of thousands of individual plants. They also require substantial land resources. Plots or greenhouses can take up thousands of acres of land. Not only does this tie up large amounts of land for months while the plants germinate, grow, and produce seed, during which time they may be sampled for laboratory or field testing, but then the massive amounts of seed must be individually tagged, harvested and processed.

A further complication is that much of the experimentation goes for naught. It has been reported in the literature that some seed companies discard 80-90% of the plants in any generation early on in the experiment. Thus, much of the land, labor and material resources expended for growing, harvesting, and post-harvest processing ultimately are wasted for a large percentage of the seed.

Timing pressures are also a factor. Significant advances in plant breeding have put more pressure on seed companies to more quickly advance lines or varieties of plants for more and better traits and characteristics. The plant breeders and associated workers are thus under increasing pressure to more efficiently and effectively process these generations and to make more and earlier selections of plants which should be continued into the next generation of breeding.

Therefore, a movement towards earlier identification of traits of interest through laboratory based seed testing has emerged. Seed is non-destructively tested to derive genetic, biochemical or phenotypic information. If traits of interest are identified, the selected seed from specific plants are used either for further experiments and advancement, or to produce commercial quantities. Testing seed prevents the need to grow the seed into immature plants, which are then tested. This saves time, space, and effort. If effective, early identification of desirable traits in seed can lead to greatly reducing the amount of land needed for experimental testing, the amount of seed that must be tested, and the amount of time needed to derive the information needed to advance the experiments. For example, instead of thousands of acres of plantings and the subsequent handling and processing of all those plants, a fraction of acres and plants might be enough. However, because timing is still important, this is still a substantial task because even such a reduction involves processing, for example, thousands of seed per day.

A conventional method of attempting non-lethal seed sampling is as follows. A single seed of interest is held with pliers above a sheet of paper laid out on a surface. A small drill bit is used to drill into a small location on the seed. Debris removed by the drill bit from the seed is collected of the sheet of paper. The paper is lifted and the debris is transferred to a test tube or other container. It is thus collected and ready for laboratory analysis. The seed is stored in another container. The two containers, housing the seed and sample, are indexed or correlated for tracking purposes. This method is intended to be non-lethal to the seed. However, the process is slow. Its success and effectiveness depends heavily on the attention and accuracy of the worker. Each single seed must be manually picked up and held by the pliers. The drilling is also manual. Care must be taken with the drilling and the handling of the debris, as well as insuring that the full sample amount is transferred into a container and the seed from which the sample was taken into another container. These two containers, e.g. the individual test tubes, must then be handled and marked or otherwise tracked and identified. Additionally, the pliers and drill must be cleaned between the sampling of each seed. There can be substantial risk of contamination by carry-over from sample to sample and the manual handling. Also, many times it is desirable to obtain seed material from a certain physiological tissue of the seed. For example, with corn seed, it may be desirable to take the sample from the endosperm. It such cases, it is not trivial, but rather is time-consuming and somewhat difficult, to manually grasp a small corn seed is such a way to allow the endosperm to be oriented to expose it for drilling. Sampling from other seed structures such as the seed germ must be avoided because sampling from such regions of the seed negatively impacts germination rates. Sometimes it is difficult to obtain a useful amount of sample with this method. In summary, sampling from seed relies heavily on the skill of the worker and is relative to throughput and accuracy, including whether the procedure gives the seed a good chance at germination. These issues are amplified when a worker is charged with processing many seed a day.

As evidenced by these examples, present conventional seed analysis methods, such as is used in genetic, biochemical, or phenotypic analysis, require at least a part of the seed to be removed and processed. In removing a portion of the seed, various objectives may need to be met. These may include one or more of the following objectives:

(a) maintain seed viability post-sampling if required;
(b) obtain at least a minimum required sample amount, without affecting viability;
(c) obtain a sample from a specific location on the seed, often requiring the ability to efficiently position and orient the seed in a specific position and orientation for sampling;
(d) maintain a particular throughput level for efficiency purposes;
(e) reduce or virtually eliminate contamination between samples;
(f) maintain an efficient and controlled post-sampling handling regimen and environment to move and collect seed portion and seed after sampling; and
(g) allow for the tracking of separate samples and their correlation to other samples in a group.

Viability

With regard to maintaining seed viability, it may be critical in some circumstances that the seed sampling method and apparatus not damage the seed in such a way that seed viability is reduced. It is often desirable that such analysis be non-lethal to the seed, or at least result in a substantial probability that the sampled seed will germinate (e.g. no significant decrease in germination potential) so that it can be grown into a mature plant. For some analyses, seed viability does not need to be maintained, in which case larger samples can often be taken. The need for seed viability will depend on the intended use of the seeds post-sampling.

Sample Amount

It is desirable to obtain a useful amount of sample. To be useful, in some applications it must be above a certain minimum amount necessary in order to perform a given test and obtain a meaningful result. Different tests or assays require different sample amounts. It may be equally important to avoid taking too much tissue for a sample, because a sample that is too large may reduce germination potential of a seed, which may be undesirable. Therefore, it is desirable that sampling apparatus, methods and systems allow for variation in the amount of sample taken from any given seed.

Sample Location

A useful sample amount also can involve sample location accuracy. For example, in some applications the sample must come only from a certain location or from certain tissue. Further, it is difficult to handle small particles like many seed. It is also difficult to accurately position and orient seed. On a corn seed, for example, it may be important to sample the endosperm tissue, and orient the corn seed for sampling that particular tissue. Therefore, it is desirable that sampling apparatus, methods and systems are adapted to allow for high throughput seed positioning and orientation of seed for location-specific sampling, which may include seed orientation apparatuses, methods and systems with architecture and steps adapted to position and orient seed in a predetermined orientation.

Throughput

A sampling apparatus and methodology must consider the throughput level that supports the required number of samples being taken in a time efficient manner. For example, some situations involve the potential need to sample thousands, hundreds of thousands, or even millions of seed per year. Taking the hypothetical example of a million seed per year, and a 5-day work week, this would average nearly four thousand samples per day for each working day of a year. It is difficult to meet such demand with lower throughput sampling methods. Accordingly, higher throughput, automatic or even semi-automatic methods are desirable.

Avoiding Contamination

It is desirable that a sampling methodology and apparatus not be prone to cross-contamination in order to maintain sample purities for subsequent analytical testing procedures. This can involve not only sample location accuracy, such that a sample from a given location is not contaminated with tissue from a different location, but also the method of sampling and the handling of each individual sample, ensuring no contamination between samples.

Handling (Post-Sampling)

With higher throughput as an objective, it is important that consideration be given to maintaining an efficient and controlled post-sampling handling regimen and environment to move and collect the seed portion and seed after sampling. Such post-sampling operations should ensure each operation is devoid of contamination. Depending on the tool used to remove a portion of the seed, such as a laser, further consideration need to be given to how the seed and seed portion are handled and collected to insure viability is preserved, contamination is limited and indexing of seed and seed portions is accurate.

Indexing (Tracking) Sample and Sampled Seed

Efficient processing of seed and samples removed from seed presents a variety of issues and challenges, especially when it is important to keep track of each seed, each sample, and their correlation to each other, or to other samples. Accordingly, it is desirable that a sampling apparatus, methods and systems allow for easy tracking of seed and samples.

Conventional seed sampling technologies do not address these requirements sufficiently, resulting in pressures on capital and labor resources, and thus illustrate the need for an improvement in the state of the art. The current apparatuses, methods and systems are relatively low throughput, have substantial risk of cross-contamination, and tend to be inconsistent because of a reliance on significant manual handling, orienting, removal and post-handling of the sample and the seed. This can affect the type of sample taken from the seed and the likelihood that the seed will germinate. There is a need to eliminate the resources current methods require for cleaning between samples. There is a need to reduce or minimize cross-contamination between samples by carry-over or other reasons, or any contamination from any source of any sample. There is also a need for more reliability and accuracy. Accordingly, there is a need for methodologies and systems and their corresponding apparatuses which provide for seed sampling that accomplishes one or more of the following objectives:

(a) maintain seed viability post-sampling if required;
(b) obtain at least a minimum required sample amount, without affecting viability;
(c) obtain a sample from a specific location on the seed, often requiring the ability to efficiently position and orient the seed in a specific position and orientation for sampling;
(d) maintain a particular throughput level for efficiency purposes;
(e) reduce or virtually eliminate contamination between samples;
(f) maintain an efficient and controlled post-sampling handling regimen and environment to move and collect seed portion and seed after sampling; and
(g) allow for the tracking of separate samples and their correlation to other samples in a group.

Some of these objectives that are desirable when sampling seed can be conflicting and even antagonistic. For example, high throughput methodologies may require relatively rapid operation but with relatively high accuracy and low contamination risk, such that they must be done more slowly than is technically possible. These multiple objectives have therefore existed in the art and have not been satisfactorily addressed or balanced by the currently available apparatuses, methods and systems. There is a need in the art to overcome the above-described types of problems such that the maximum number of objectives is realized in any given embodiment.

BRIEF SUMMARY OF THE INVENTION

Apparatuses, methods and systems for positioning, orienting, creating, handling, collecting, and indexing seed portions, including viable seed portions, from plant seed is disclosed. In one general example of the apparatus, the apparatus includes a carrier having a feature for positioning and orienting seed, a seed portion or the like. Seed portions may be taken from seed in carrier. One or more manifolds aid in separating, collecting and indexing seed and seed portions in an efficient and high throughput manner.

A general example of a method for positioning, orienting, creating, handling, collecting, and indexing seed portions, including viable seed portions, from plant seeds is also disclosed. The method may include positioning and orienting seed relative to carrying positions within a carrier, ablating the seed with a seed ablation device, separating, collecting and indexing seed and seed portions using a manifold in a collector and compartment layer.

A general example of a system for positioning, orienting, creating, handling, collecting, and indexing seed portions, including viable seed portions, from plant seeds is also disclosed. The system may include a carrier adapted to retain seed in a desirable position and orientation, a seed ablation device, a manifold adapted to handle, collect and index seed and seed portions (post-sampling) into one or more containers.

BRIEF DESCRIPTION OF THE DRAWINGS

FIG. 5A is an isometric view of the carrier according to an exemplary embodiment of the present invention.

FIG. 5B is a cross-section view of the carrier taken along line 5B-5B in FIG. 5A.

FIG. 8A is an isometric view of a spacer plate according to an exemplary embodiment of the present invention.

FIG. 9A is an isometric view of a reducer plate according to an exemplary embodiment of the present invention.

FIG. 9B is a plan view of the spacer plate shown in FIG. 9A.

FIG. 9C is a section view taken along line 9C-9C in FIG. 9B.

FIG. 10A is an isometric view of the another manifold according to an exemplary embodiment of the present invention.

FIG. 10B is a top view of the manifold shown in FIG. 8A.

FIG. 10C is a bottom view of the manifold shown in FIG. 8A.

FIG. 11A is an isometric view of the collector according to an exemplary embodiment of the present invention.

DETAILED DESCRIPTION OF THE EXEMPLARY EMBODIMENTS

Overview

Figure 1:
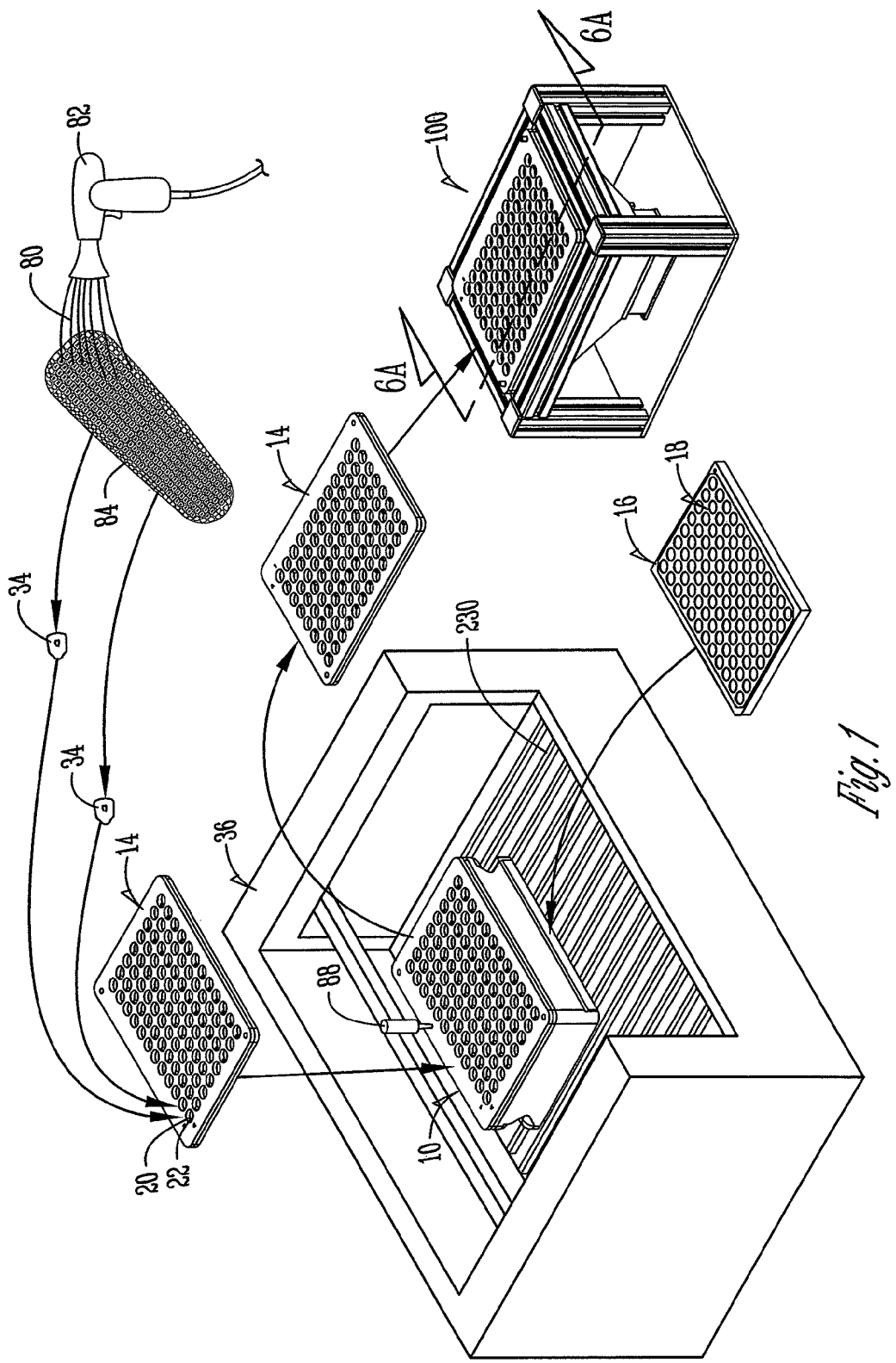
FIG. 1 is an overview of the apparatuses, methods and systems used for creating viable seed portions from plant seeds according to an exemplary embodiment of the present invention.

For a better understanding of the invention, several exemplary embodiments will now be described in detail. It is to be understood that these are but several forms the invention can take and do not limit the invention. Reference will be taken from time-to-time to the appended drawings. Reference numerals are used to indicate certain parts and locations in the drawings. The same reference numerals will indicate the same parts and locations throughout the drawings unless otherwise indicated.

The context of these specific examples will be with respect to kernels of corn. It is to be understood, however, that this example is only intended to illustrate one application of the invention. The invention can be utilized for other seed and other objects. The range of sizes can vary as well as the nature of the object. As will be understood by one of skill in the art, the embodiments of the invention will be used with seed that are of convenient size to be sampled. Some seed are extremely fine and small, somewhat like dust particles or grains of salt, while others are particularly large and hard, such as the seed from the *Lodoicea maldivica* palm, which are 20 to 24 pounds in weight. One of skill in the art recognizes that seed intended to be used with the embodiments of the invention must be of a size and weight that allow convenient sampling with the apparatus of the embodiments. Such seed include, but are not limited to, many agriculturally important seed such as seed from maize (corn), soybean, *Brassica* species, canola, cereals such as wheat, oats or other grains, and various types of vegetable and ornamental seed. Analogous applications will be obvious from this example and variations obvious to those skilled in the art will be included.

Reference will be made to samples taken from a seed as seed portions. The seed portion that has been taken can also be referred to using different terms, such as, for example, seed sample, seed tissue sample, seed chip, seed snip, seed sliver, seed clip or clipping, and viable seed portion.

Apparatus

FIG. 1 illustrates many different exemplary apparatuses of the present invention for positioning and orienting seed for creating, partitioning, sorting, handling, collecting and indexing seed and viable seed portions or the like from plant seed. The apparatuses in FIG. 1 teach in the broadest sense, structure adapted to position and orient seed in a predetermined orientation so that an operation to remove a seed portion from each seed may be accomplished in an efficient, non-lethal, non-contaminating and high throughput manner. Some other structure, or the same structure used to position and orient seed, may also be used to handle the seed and seed portions (post-sampling) in an efficient, non-lethal, non-contaminating and high throughput manner. These same structures or some additional structure may be also be used to index or correlate seed and seed portions in an efficient, non-lethal, non-contaminating and high throughput manner.

Figure 2:
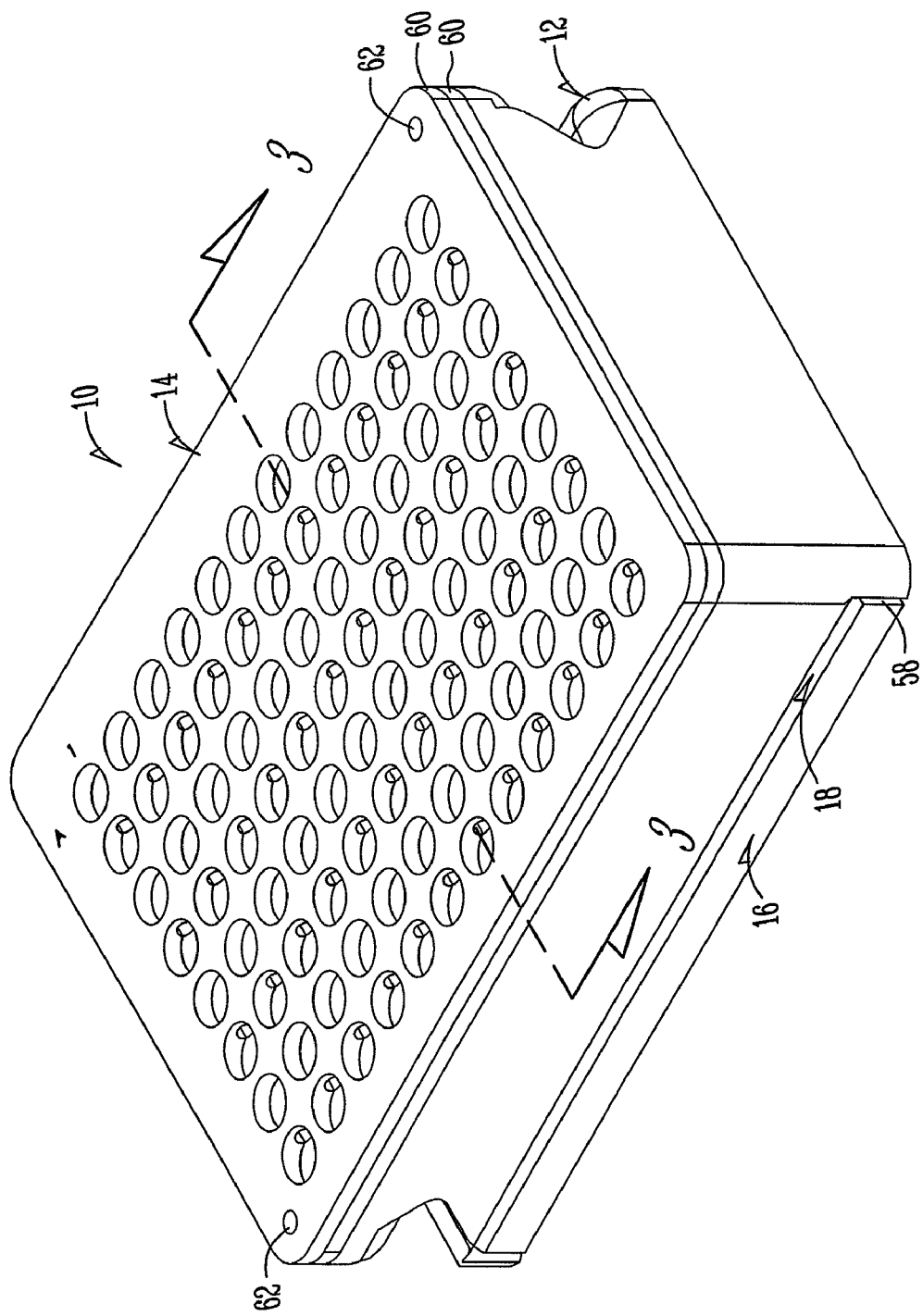
FIG. 2 is an isometric view of the manifold, carrier, compartment layer, and jig assembled together according to an exemplary embodiment of the present invention.
Figure 12:
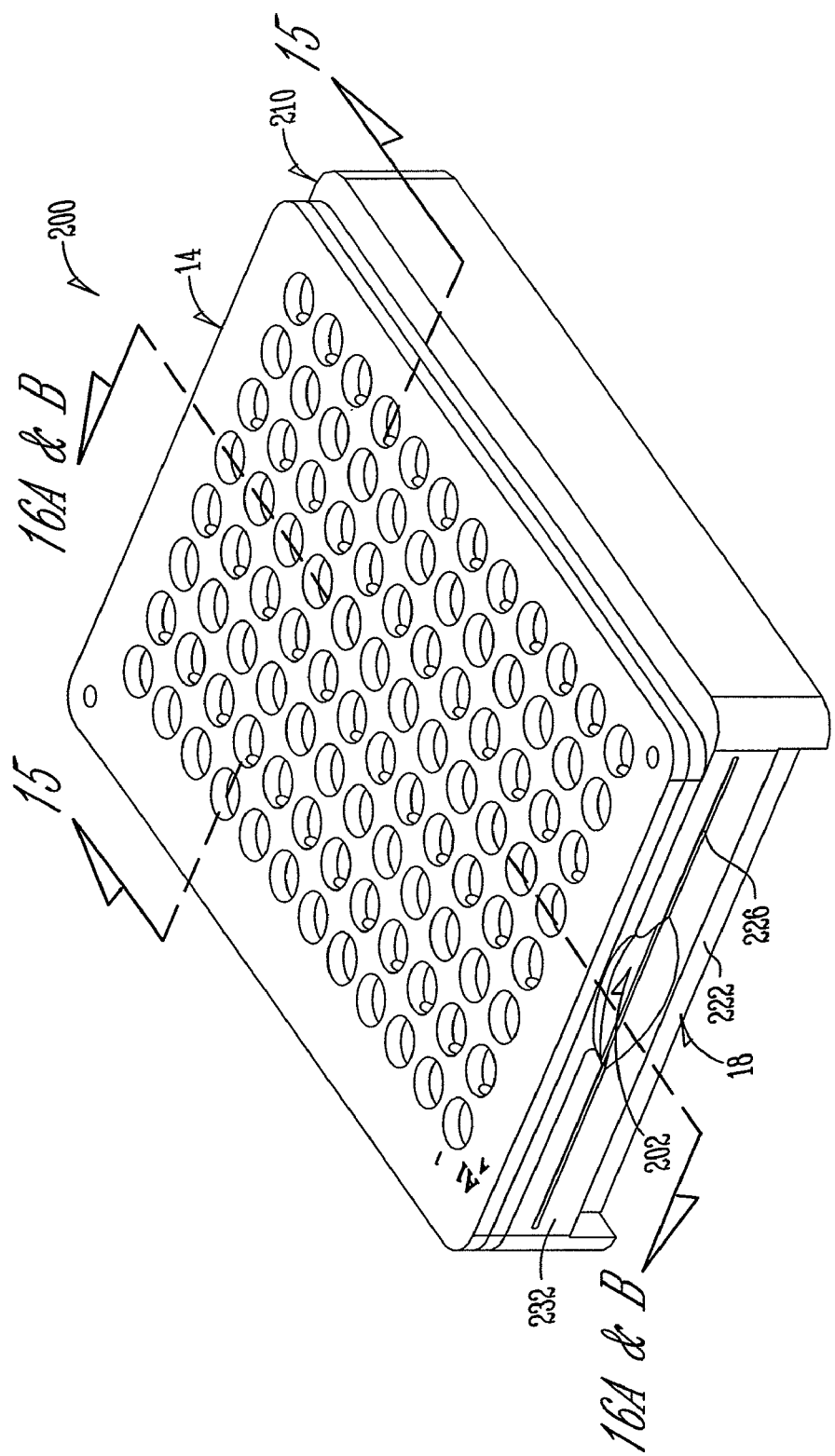
FIG. 12 is an isometric view of the carrier and another manifold according to an exemplary embodiment of the present invention.

Generally illustrated in FIG. 1, by way of exemplary apparatuses, is apparatus 10 having a manifold 12, carrier 14, jig 16, and compartment layer 18. Apparatus 10 is best illustrated in FIGS. 2-5B. FIG. 12 shows another apparatus 200 having another manifold 210 with the aforementioned carrier 14 and configured with a slot 222 to accommodate jig 16 and compartment layer 18 within the body of manifold 210. Details and description for manifold 10 will follow with details and description for manifold 210 thereafter. According to one general aspect of the present invention, apparatus 10 may include a carrier 14. Carrier 14 is best illustrated in FIGS. 2, 5A and 5B. Carrier 14 is preferably a planar member and may be constructed of plate members 60. Carrier 14 may be constructed of a single unitary plate member 60 or a pair of plate members 60 sandwiched together to form the carrier 14. In the preferred embodiment, carrier 14 is constructed or fabricated of a material capable of withstanding any erosional, degradative or destructive properties associated with various methods used for seed ablation. For example, carrier 14 may be fabricated of a metal alloy, steel, composite material, or the like.

Carrier 14 has a plurality of apertures 20 formed through plate member(s) 60. In a preferred form, each aperture 20 is formed so as to pass through the entirety of the plate member (s) 60. It should be appreciated by those skilled in the art that apertures 20 need not pass through the entirety of plate member(s) 60. For example, if a pair of plate members 60 are used, aperture 20 could pass through the entirety of the uppermost plate and a portion of the lower plate to form a pocket in the lower plate whereby seed and seed portions may be housed in the uppermost plate and collected in the pocket in the lower plate as desired. In another embodiment, the lower plate could be adapted to selectively move a planar gate relative to apertures 20 to present an open and closed aperture 20. In the closed position, seed and seed portions could be collected in the lower plate; alternatively, in the open position, seed and seed portions could be released from or communicated through the lower plate. The aperture 20 may be formed in the carrier 14 by drilling, machining, etching, or any other technique suitable for creating the plurality of apertures 20 in a predictable, pattern-like formation. For example, the plurality of apertures 20 may be formed in a row 28, column 30 formations whereby each aperture 20 is uniquely identifiable and/or positionally addressable. Alternatively, a single oblong aperture or a set of oblong apertures may be fashioned into carrier 14 by row or columns to provide single or multiple channels adapted to carry one or more seeds or seed portions. FIG. 5A shows carrier 14 in a twelve (12) aperture/row by eight (8) aperture/column configuration for a total of ninety-six (96) apertures. It should be appreciated that carrier 14 is not limited to the configuration shown in the drawings. Alternative configurations, not limited to row, column or specific number of apertures 20, could be used as best suited for the various applications.

Each aperture 20 is preferably formed having one or more carrying position(s) 22. Each carrying position 22 is adapted to house, receive, orient or position seed 34 relative to some local or global coordinate relative to the carrying position 22 and/or carrier 14. For example, each seed 34 could be oriented relative to a sidewall 26 of aperture 20. The carrying position 22 may be specially shaped to the contour of seed 34 or otherwise to aid in orienting seed 34 at carrying position 22. In another aspect of the present invention, a seed orienter 24 may be associated with each aperture 20 orient seed 34 or govern the orientation of seed 34 relative to each carrying position 22. FIG. 5B shows a magnet positioned between sidewall 26 of a pair of apertures 20. The magnet is one example of a seed orienter 24 suitable for orienting seed 34. Each aperture 20 could be configured with a magnet or share a magnet with another aperture as shown in FIG. 5B. Alternatively, the seed orienter 24 may be a separate or different material than plate member(s) 60 whereby the seed orienter 24 exhibits retentive-like properties capable of adhering to or retaining seed 34 at a specific position relative to aperture 20. For example, vacuum ports, grippers or any type of sticky or self adhering surface could be incorporated into each aperture 20 to retain and orient seed 34. In sum, the carrier 14 provides a self-aligning, self-orientating, and self-positioning feature whereby each seed 34 may be identically positioned, aligned or oriented in a carrying position 22 relative to one or more features of the carrier 14, such as sidewall 26 of each aperture 20. For example, it may be said that carrier 14 provides fixturing or a jig for receiving, handling, orienting, and retaining seed 34 at a specific, predictable, and desired space or location relative to carrier 14.

According to a further aspect of the present invention, carrier 14 is constructed so as to be portable. In another aspect of the present invention, carrier 14 is fashioned so as to be dockable on another structure such as manifold 12, shown in FIGS. 2 and 3, manifold 102, shown in FIGS. 6A, 7C, 10AC, or manifold 210, shown in FIG. 12. To facilitate docking, more specifically, aligning, carrier 14 relative to manifold 12, 102, aperture 62, formed through carrier 14, mates with alignment pin 66, 112 in manifold 12, 102 to thereby orient carrier 14 relative to manifold 12, 102 to dock carrier 14 with manifold 12, 102. Alternatively, aperture 68, 114 may be formed in manifold 12, 102. Apertures 68, 114 may be adapted to receive and house alignment pins 66, 112. Alignment pins 66, 112 may be positioned through apertures 62 in carrier 14 to thereby orient and dock carrier 14 with manifold 12, 102. In another aspect of the present invention, alignment pins 66, 112 may be removable from aperture 68, 114 and/or may be formed as a single unitary piece with carrier 14 or manifold 12, 102. The present invention contemplates that manifold 12, 102 could include, separately or in addition to alignment pins 66, 112 in manifold 12, 102, an extruded boss to positively position carrier 14 with respect to manifold 12, 102 when the two are docked together.

Figure 3:
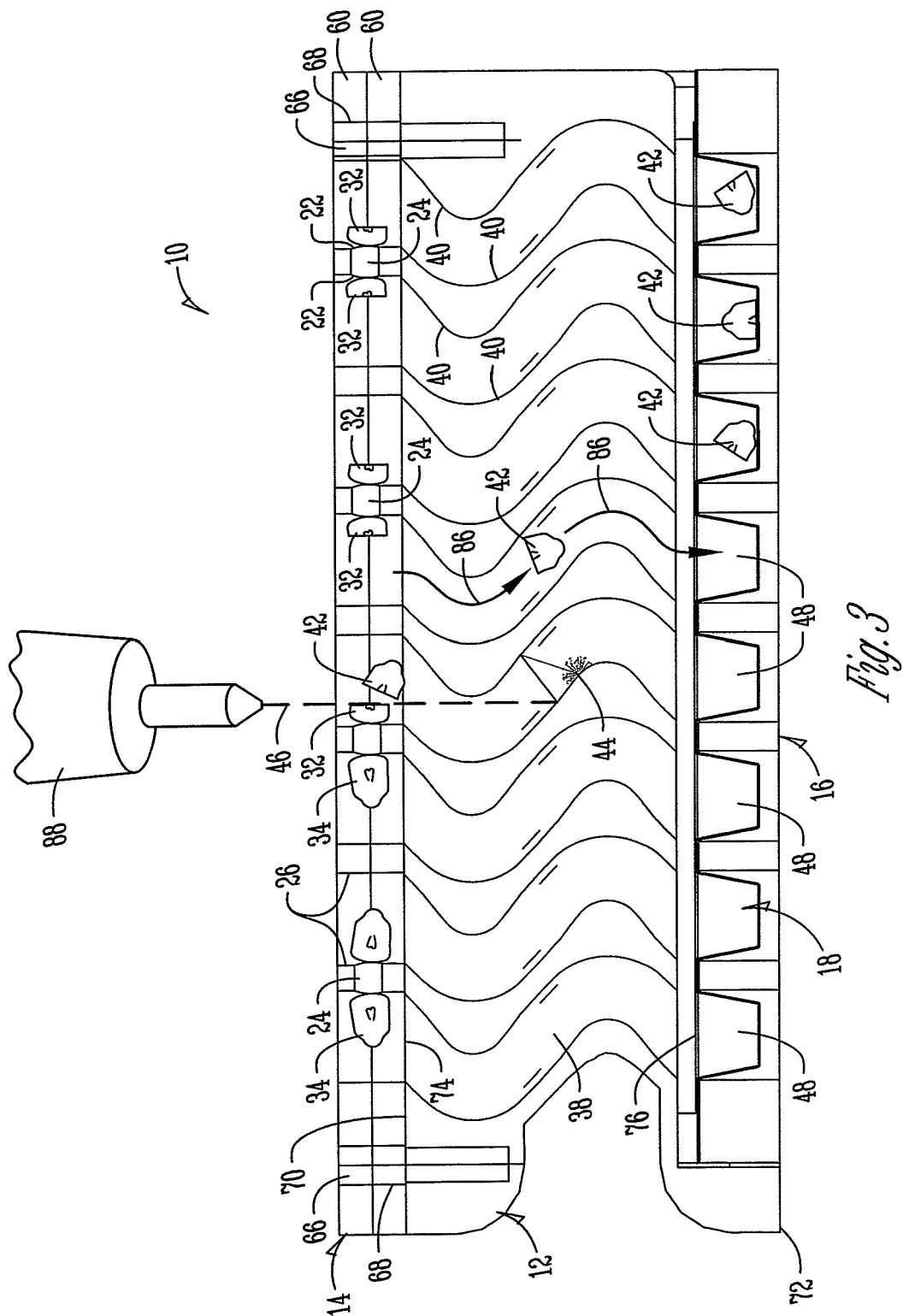
FIG. 3 is a cross-sectional view taken along line 3-3 in FIG. 2.

FIGS. 2 and 3 best illustrate one exemplary embodiment of manifold 12 of the present invention. Similar to carrier 14, manifold 12 may be constructed from like materials. Preferably, manifold 12 has a top surface 70 suitable to dock carrier 14 thereupon. Considerations may be given to the bottom surface 72 of manifold 12 to facilitate docking manifold 12 within an ablation device, such as the ablation device 36 shown in FIG. 1. For example, bottom surface 72 of the manifold 12 may include self-leveling and/or self-aligning features, whereby manifold 12 may be aligned or leveled relative to the ablation device 36 or other local and/or global coordinates. One or more self-positioning, aligning or leveling plates (not shown) may be included for use in self-positioning, aligning and/or leveling manifold 12 relative to the support deck of the ablation device 36. For example, the plate could be milled with a slight pitch which causes manifold 12 to automatically slide into a desired position within and relative to ablation device 36 to thereby ensure ablation consistency.

As best illustrated in FIG. 3, manifold 12 has a plurality of conduits 38 extending there through from top surface 70 through bottom surface 72. In the preferred form, each inlet 74 of the plurality of conduits 38 in manifold 12 has the same pattern, size and shape as the plurality of apertures 20 in carrier 14. Thus, inlet 74 of each conduit 38 in manifold 12 mates, aligns, and is in communication with aperture 20 in carrier 14 to allow uninterrupted transfer of seed portions 42 through aperture 20 into conduit 38 in manifold 12.

Each conduit 38 has sidewalls 40. Sidewalls 40 could be linear and cylindrical whereby energy from the ablation device 36 passes through the entirety of manifold 12 and diffuses within the ablation device 36. Compartment layer 18 could be inserted after ablation to prevent any damage to the compartment layer 18. In a preferred form, sidewalls 40 are contoured or shaped so as to diffuse energy from the ablation device 36 to prevent energy beam 46 from traveling intact from the inlet 74 of the conduit 38, through the conduit 38 and outlet 76. For example, as shown in FIG. 3, sidewalls 40 of conduit 38 in manifold 12 are contoured in shape so that energy beam 46 from ablation device 36 is reduced to diffracted energy 44 or diffused to prevent energy beam 46 from traveling intact through the conduit 38 and out outlet 76. In one aspect, sidewalls 40 of each conduit may be fashioned in a cylindrical, helical, conical, or other shape to sufficiently diffuse energy from the ablation device 36. The present invention contemplates other diffusion techniques. For example, sidewall 40 or a portion thereof could be made to be coarse, as opposed to being smooth, to diffuse energy from the ablation device 36. Sidewall 40 or a portion thereof could also be coated or anodized to thereby diffuse or absorb energy from the ablation device 36. Abutments or projections originating in sidewall 40 and extending into conduit 38 could also serve to diffuse energy, but not interrupt the communication of seed and seed portions through manifold 12. Thus, as energy beam 46 from ablation device 36 travels through aperture 20 and carrier 14, energy beam 46 is deflected and diffracted off of and between sidewalls 40 of conduit 38 to sufficiently diffuse energy from the ablation device 36 to prevent destruction, damage, or failure of compartment layer 18, as well as damage to seed or seed portions to maintain viability.

In another aspect of the present invention, each outlet 76 of each conduit 38 in manifold 12 is open to a slot 58 near the bottom surface 72 of manifold 12. The slot 58 in manifold 12 is fashioned so as to receive compartment layer 18 supported by jig 16, as best illustrated in FIGS. 2 and 3. Compartment layer 18 has a plurality of compartments 48 which preferably exhibit the identical pattern of the plurality of conduits 38 in manifold 12 and the plurality of apertures 20 in carrier 14. Furthermore, the plurality of compartments 48 in compartment layer 18 may each be uniquely identifiable and/or positionally addressable by row 54 and column 56 as best illustrated in FIG. 4C. Like carrier 14, compartment layer 18 is not limited to the configuration shown in FIG. 4C. The present invention contemplates compartment layer 18 taking on various configurations best suited for the specific application. By way of example, compartment layer 18 could be modeled to conform to the various shapes, configurations or designs of carrier 14. Alternatively, compartment layer 18 could be shaped and configured, unlike carrier 14, with emphasis given to post-handling considerations after removal of compartment layer 18 from the manifold 12. Although not shown, manifold 12 may also include a clip or other attachment means that could be used to hold seed ID information. This is useful because information about the seed stays with the seed during the entire process until it may ultimately be used to label both the compartment layer 18 containing the sampled seed and collector 104 having the seed samples. The top surface 122 of manifold 12 may also include a small tray-like groove (not shown). The tray-like groove may be used to hold a portion or reserve of extra seed that came from the same source as the seed being sampled. This way manual sampling of seed from this small batch could occur, allowing the process of ablation and collection to continue, if the user approaches the end of the ablation and collection process and there are sampled seed or samples of seed that are missing. This maintains process flow by eliminating the need for the operator or user to track back to the source of seed being sampled when the user is near the end of the process. The small batch of seed can in most cases be disposed of if not used.

Figure 4A:
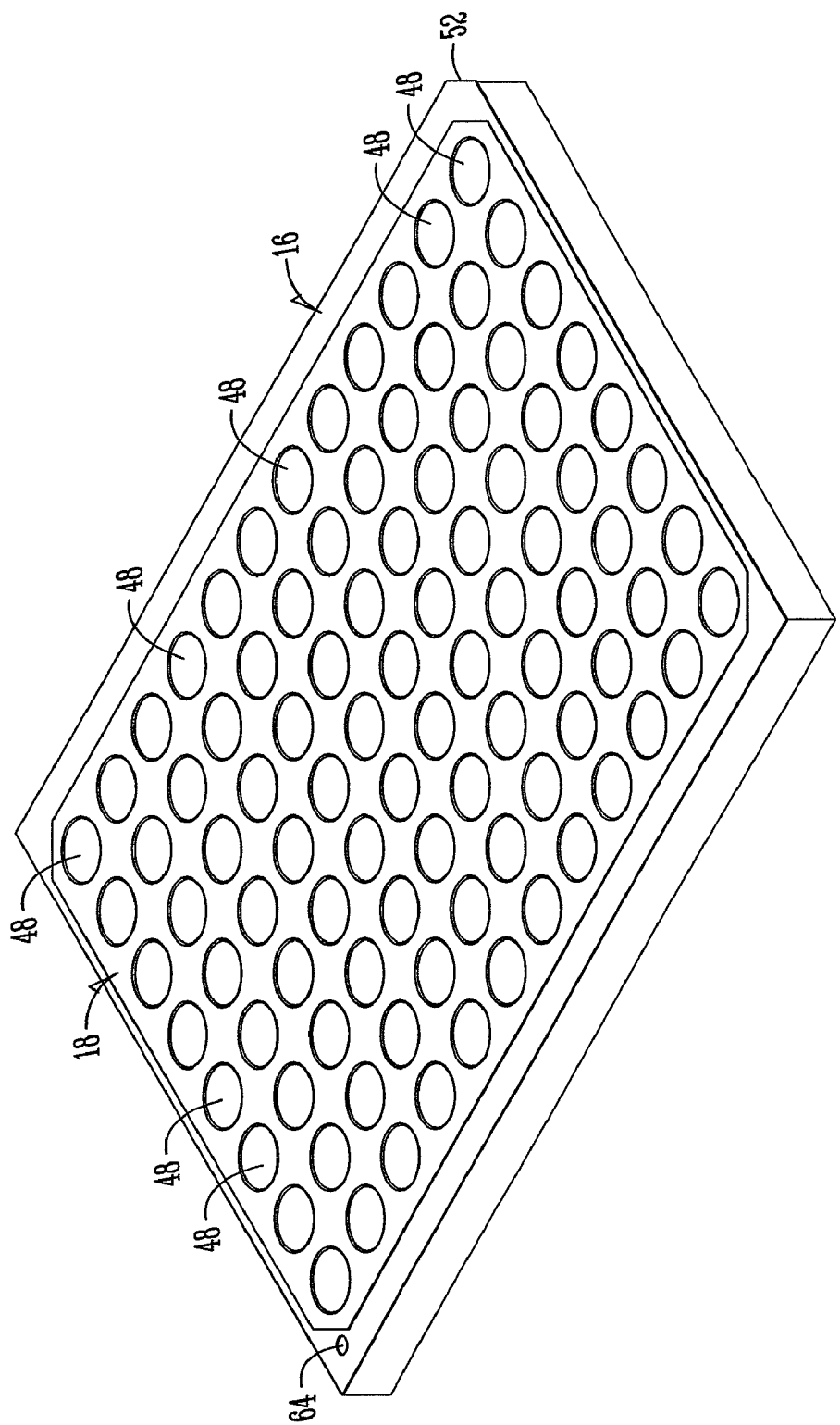
FIG. 4A is an isometric view of the compartment layer and jig according to an exemplary embodiment of the present invention.
Figure 4B:
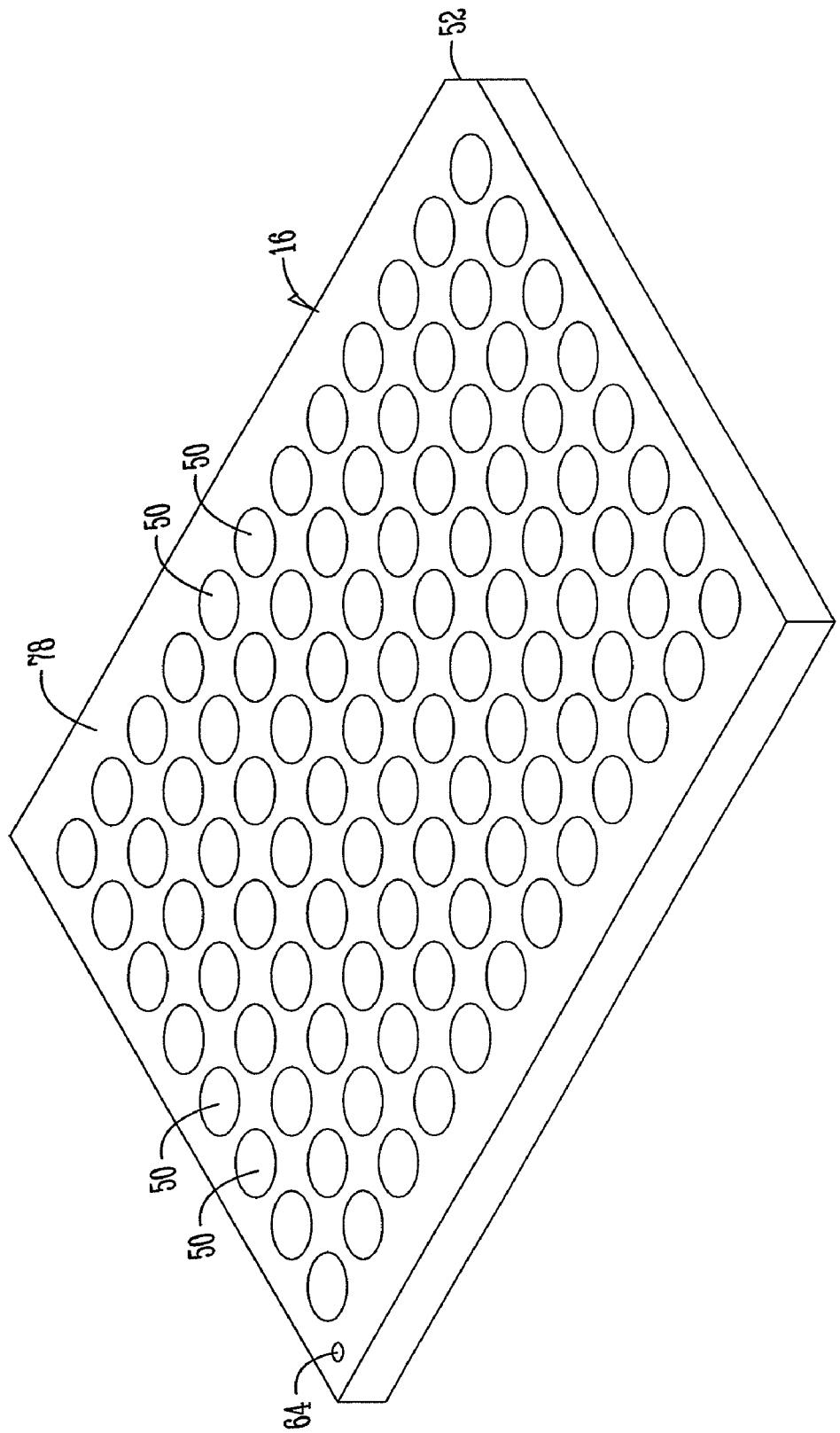
FIG. 4B is an isometric view of the jig according to an exemplary embodiment of the present invention.
Figure 4C:
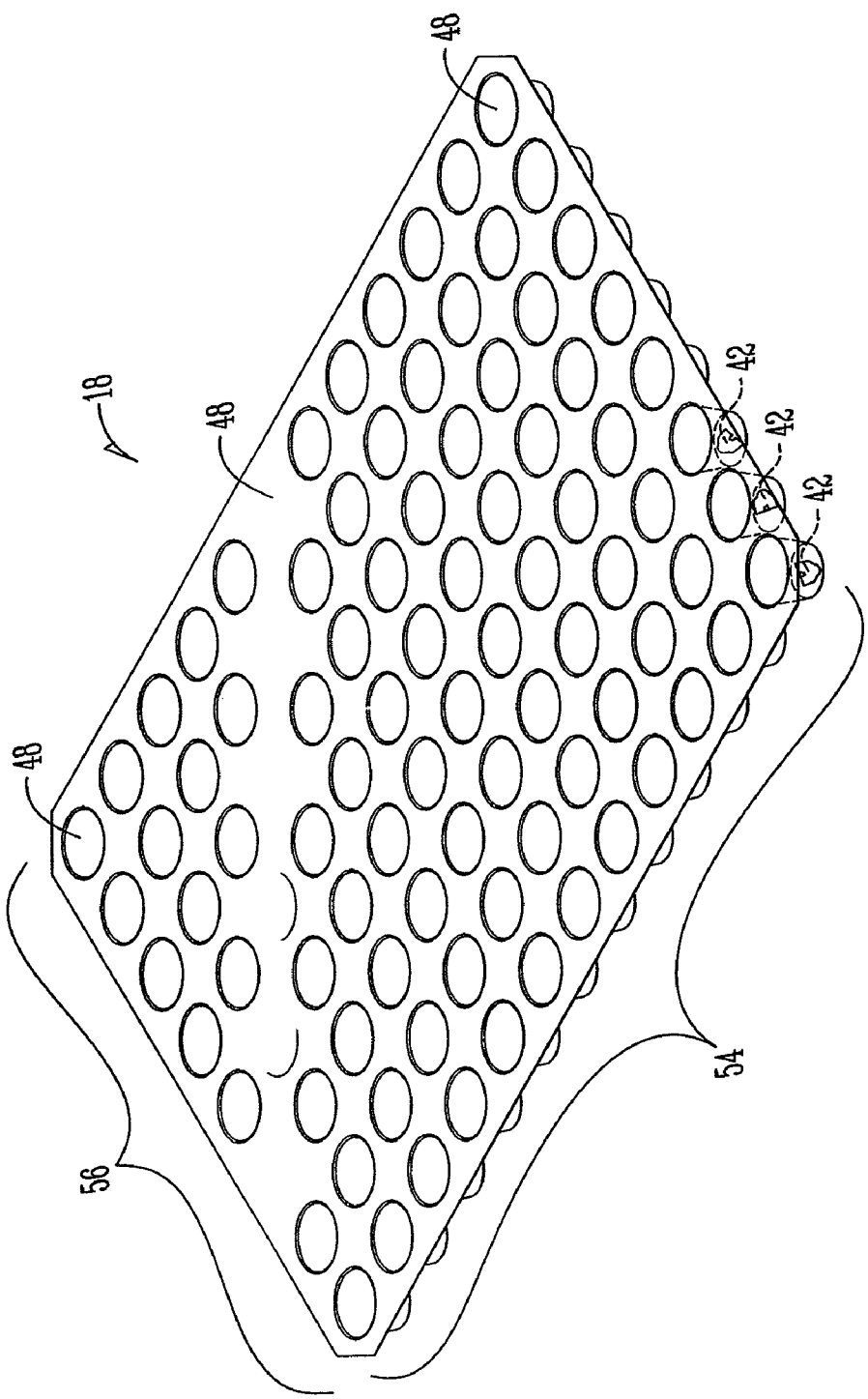
FIG. 4C is an isometric view of the compartment layer according to an exemplary embodiment of the present invention.

Jig 16 as shown in FIG. 4B has a plurality of apertures 50 exhibiting the same identical pattern of the plurality of compartments 48 of the compartment layer 18. Thus, in the preferred form, jig 16 is adapted to receive compartment layer 18 whereby compartment layer 18 is positioned on the top 78 of jig 16 with the plurality of compartments 48 of the compartment layer 18 being received within the plurality of apertures 50 in the jig 16. Jig 16 may be made up of one or more layers of the same or differing materials to facilitate better fit between the top 78 of jig 16 and compartment layer 18. Additional layers could also be of material types providing a better and more even support base for compartment layer 18. For example, a layer of felt, such as a ⅛" thick layer of F-13 felt, could be added to the top 78 of jig 16. The layer of felt could be used to help facilitate a more even seal across the entire compartment layer 18, such as during a heat sealing a backing to compartment layer 18. Other positionally adjustable and/or orientative features may also be configured into jig 16. Jig 16 may have one or more corners having a notch 52 and/or aperture 64. These features 52, 64 may be used to orient jig 16 within slot 58 of the manifold 12, orient compartment layer 18 relative to jig 16 and/or orient compartment layer 18 and jig 16 relative to some other structure and/or apparatus used to facilitate purposes befitting of the compartment layer 18 or the jig 16. Positioned within slot 58 in manifold 12, the plurality of compartments 48 of compartment layer 18 are aligned with the outlet 76 of the plurality of conduits 38 in the manifold 12. Thus, when carrier 14 is docked on manifold 12 and compartment layer 18 is positioned within slot 58, a throughway 86, as shown in FIG. 3, is formed from aperture 20 in carrier 14 through inlet 74 and conduit 38, out outlet 76 into compartment 48 within compartment layer 18. Using throughway 86, seed portion 42 formed from ablating seed 34 is communicated from aperture 20 in carrier 14 through conduit 38 in manifold 12 into compartment 48 in compartment layer 18, as best illustrated in FIG. 3. Retained seed portions 32 may be held at their respective carrying position 22 within aperture 20 of carrier 14 by a seed orienter 24. Carrier 14 may be undocked or removed from manifold 12. In the preferred form, carrier 14 is undocked or removed from manifold 12 having retained seed portions 32 at each carrying position 22 within aperture 20 of the carrier 14.

FIG. 1 illustrates one embodiment of the ablation device 36 of the present invention. Ablation device 36 is of the type which is commercially available. Ablation device 36 has a bed 230 supporting apparatus positioned within the ablation device 36. Bed 230 may be configured to dissipate the laser and prevent the laser from being reflected in undesirable directions. For example, laser beam from laser 88 may travel through a 2" honeycomb layer and onto a black anodized tray at the bed 230 of the ablation device 36. It may be approximately 3-4" below the honeycomb where the manifold 210 actually rests upon some supporting structure in bed 230. One example of an ablation device 36 could be a 75 watt Epilog 36 EXT laser CO2 engraving, cutting, and marking system available at Epilog Laser • 16371 Table Mountain Parkway • Golden, Colo. 80403.

Figure 6A:
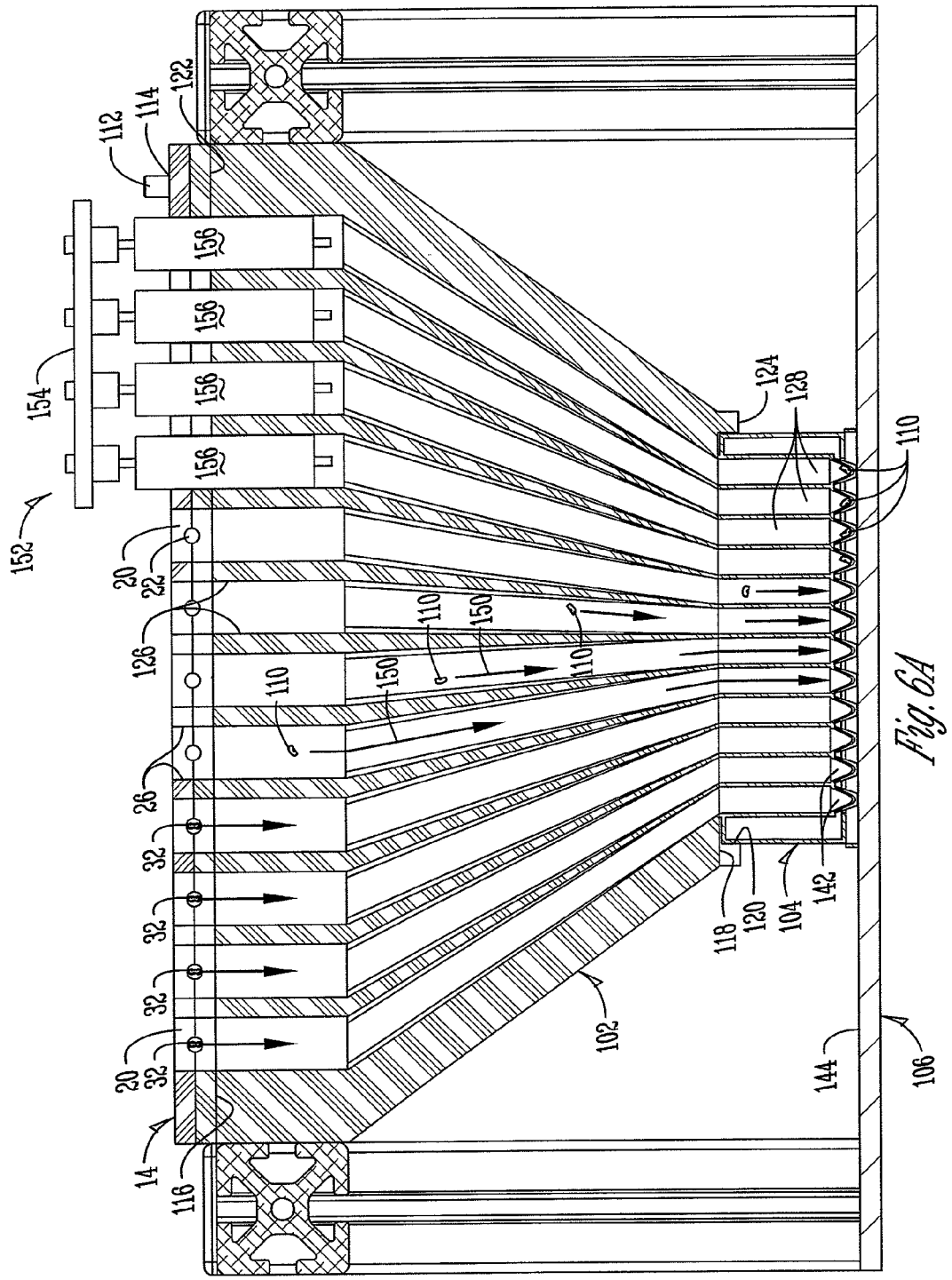
FIG. 6A is a cross-section view taken along line 6A-6A in FIG. 1.

FIGS. 1 and 6A illustrate another apparatus 100 of the present invention. Apparatus 100 has a manifold 102 in communication with a collector 104 retained by a frame 106. Frame 106 may be supported by base 144. Similar to manifold 12, manifold 102 may have one or more pins 112 positioned within apertures 114 and adapted to facilitate aligning, orienting, or docking carrier 14 on top surface 122 of manifold 102. Thus, carrier 14 may be undocked from manifold 12 and redocked on manifold 102. Illustrated by FIGS. 10A-10C, manifold 102 configured with a plurality of conduits 108 extending through the body of manifold 102 from top surface 122 to bottom surface 124. Thus, the plurality of conduits 108 extending through the body of the manifold 102 have an inlet 146 at the top surface 122 and an outlet 148 at the bottom surface 124. Furthermore, as best illustrated in FIG. 6A, a portion of the manifold 102 near the top surface 122 has a larger cross-sectional area 116 which tapers in a hopper-shape-like manner to a smaller cross-sectional area 118 near the bottom surface 124 of the manifold 102. Each of the plurality of conduits 108 extending through manifold 102 have sidewalls 126 which preferably taper to follow the contour of the body of the manifold 102 from the larger cross-sectional area 116 to the smaller cross-sectional area 118. In another aspect of the present invention, the plurality of conduits 108 may have a continually narrowing cross-sectional area or tapering sidewall 126 from the top surface 122 to the bottom surface 124 of the manifold 102. Similar to manifold 12, the plurality of conduits 108 in manifold 102 have an identical pattern as the plurality of apertures 20 in carrier 14 so that the plurality of apertures 20 in carrier 14 are in communication with the plurality of conduits 108 in manifold 102. It is preferred that the manifold 102 is supported by frame 106 so that carrier 14 may be docked and undocked from manifold 102.

Figure 11B:
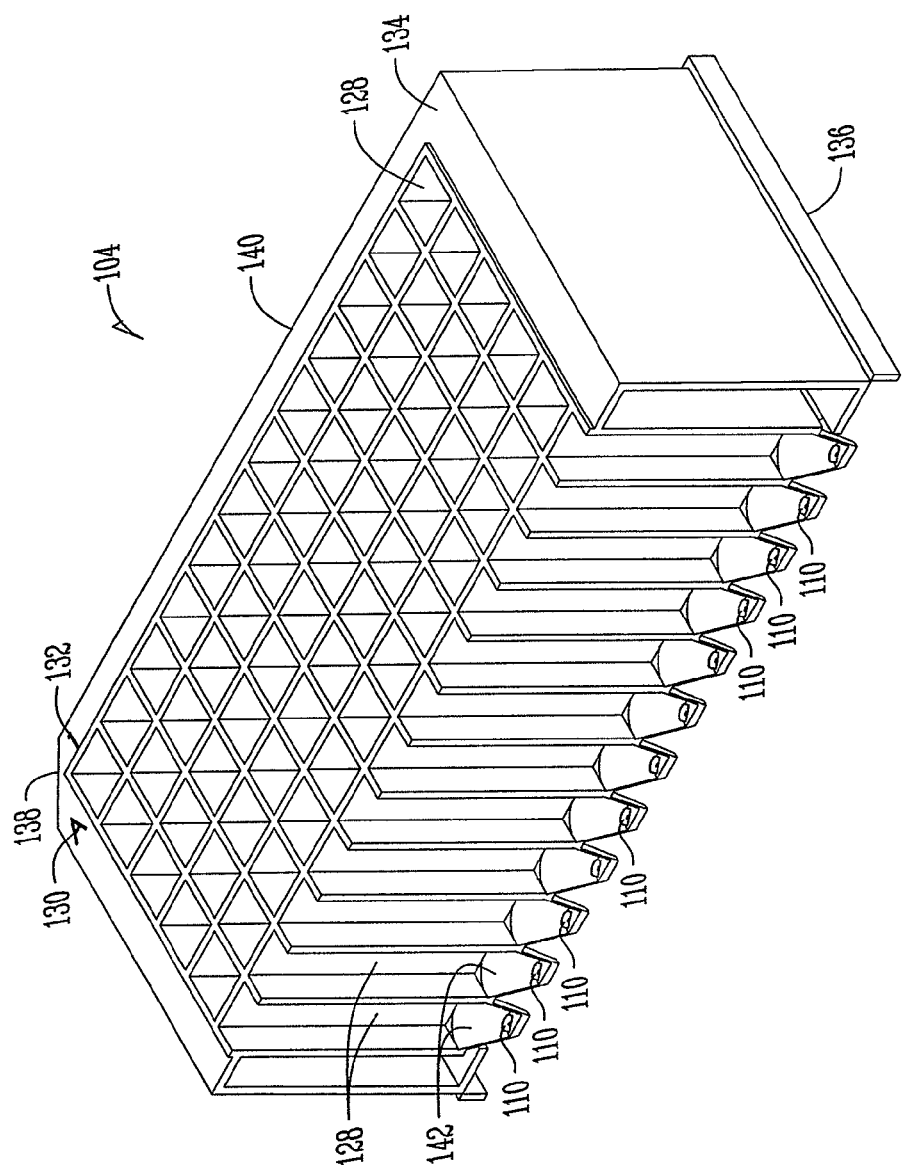
FIG. 11B is a cross-sectional view of the collector taken along line 11B-11B in FIG. 11A.

In another aspect of the present invention, manifold 102 has a slot 120 fashioned in the bottom surface 124. Slot 120 formed in the bottom surface 124 of manifold 102 receives and houses collector 104. As best illustrated in FIGS. 11A and 11B, collector 104 has a plurality of compartments 128. In the preferred form, the plurality of compartments 128 in the collector 104 are open at the top surface 134 and closed at the bottom surface 136. The plurality of compartments 128 in collector 104 are in communication with the outlet 148 of the plurality of conduits 108 near the bottom surface 124 of manifold 102. Each compartment 128 may be uniquely identifiable and/or positionally addressable by row 130 and column 132 or otherwise. Collector 104 may have orienting and/or position indicating features such as notched corner 138. Notched corner 138 may be used to correctly orient and position collector 104 within slot 120 of manifold 102 so that the plurality of compartments 128 are in communication with the plurality of conduits 108 at the outlet 148 of manifold 102 when collector 104 is positioned within slot 120 as shown in FIG. 6A. Furthermore, the outer perimeter 140 of collector 104 may be bounded and guided by slot 120 in manifold 102 to correctly position and orient collector 104 within slot 120 of manifold 102. In another aspect of the present invention, a well 142 may be fashioned within a bottom portion of each compartment 128 of collector 104. Well 142 may be shaped so as to contain seed portion 110 for collection, retention, testing or otherwise. When collector 104 is positioned within slot 120 of manifold 102, as shown in FIG. 6A, retained seed portion 32 may be communicated from aperture 20 in carrier 14 through conduit 108 in manifold 102 into compartment 128 in collector 104 along throughway 150. The retained seed portion 32 within aperture 20 of carrier 14 is shown as seed 110 being communicated through conduits 108 of the manifold 102 into well 142 within compartments 128 of collector 104. Each seed portion 110 within each compartment 128 of collector 104 may be uniquely identifiable and/or positionally addressable so as to coordinate with each uniquely identifiable and/or positionally addressable carrying position 22 in carrier 14. Thus, it is preferred that each compartment 48, 128 in compartment layer 18 and collector 104 may be uniquely identifiable and/or positional addressable by coordinating these positions with the carrying position 22 in the carrier 14 so that viable seed portion 42 within compartment 48 of compartment layer 18 and seed portion 110 within compartment 128 of collector 104 may be correlated and traced back to the original seed 34 positioned within carrier 14 at each carrying position 22 uniquely identified and/or positioned addressable by a row/column system or otherwise.

Figure 6B:
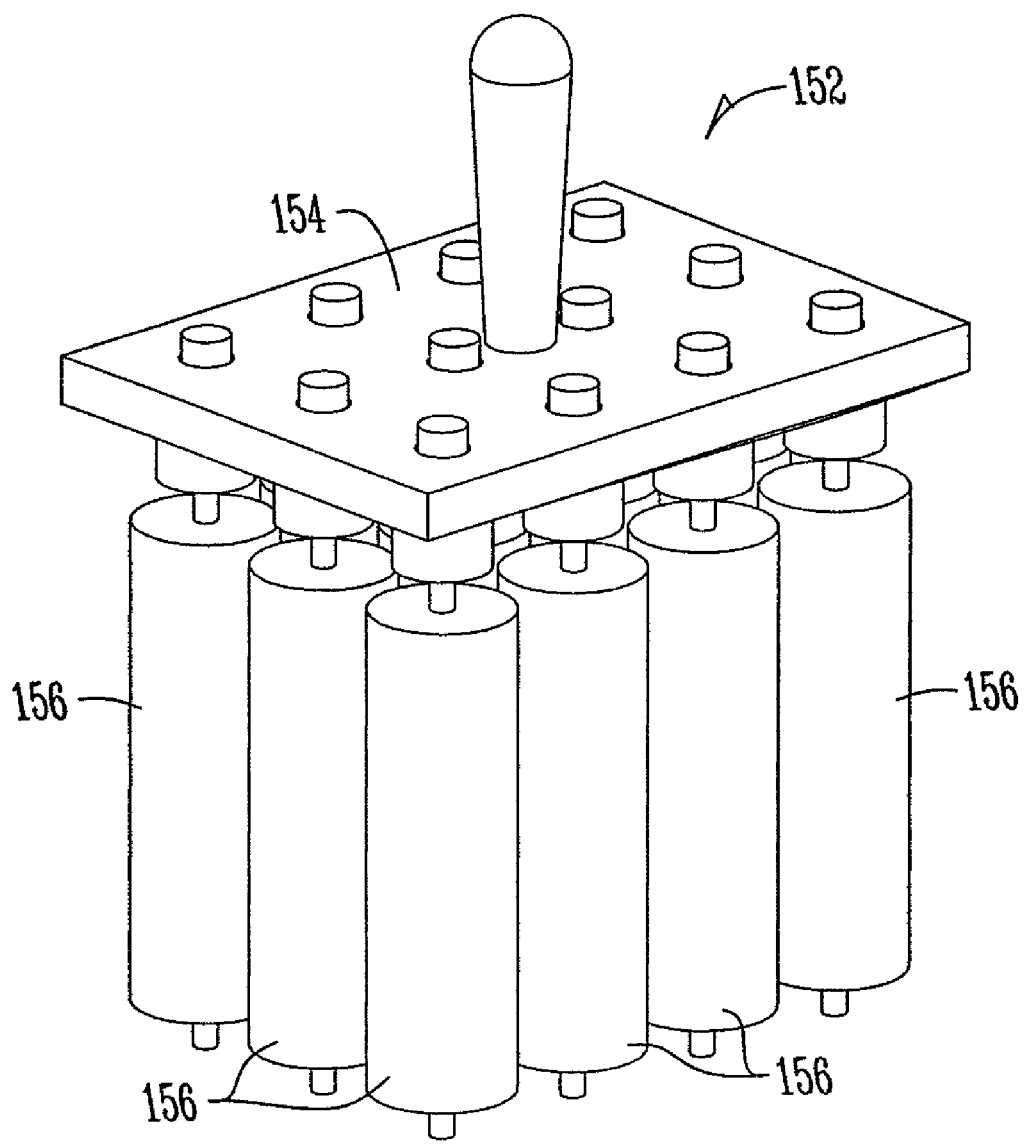
FIG. 6B is an isometric view of one example of a tool for displacing retained seed portions shown in FIG. 6A.
Figure 7A:
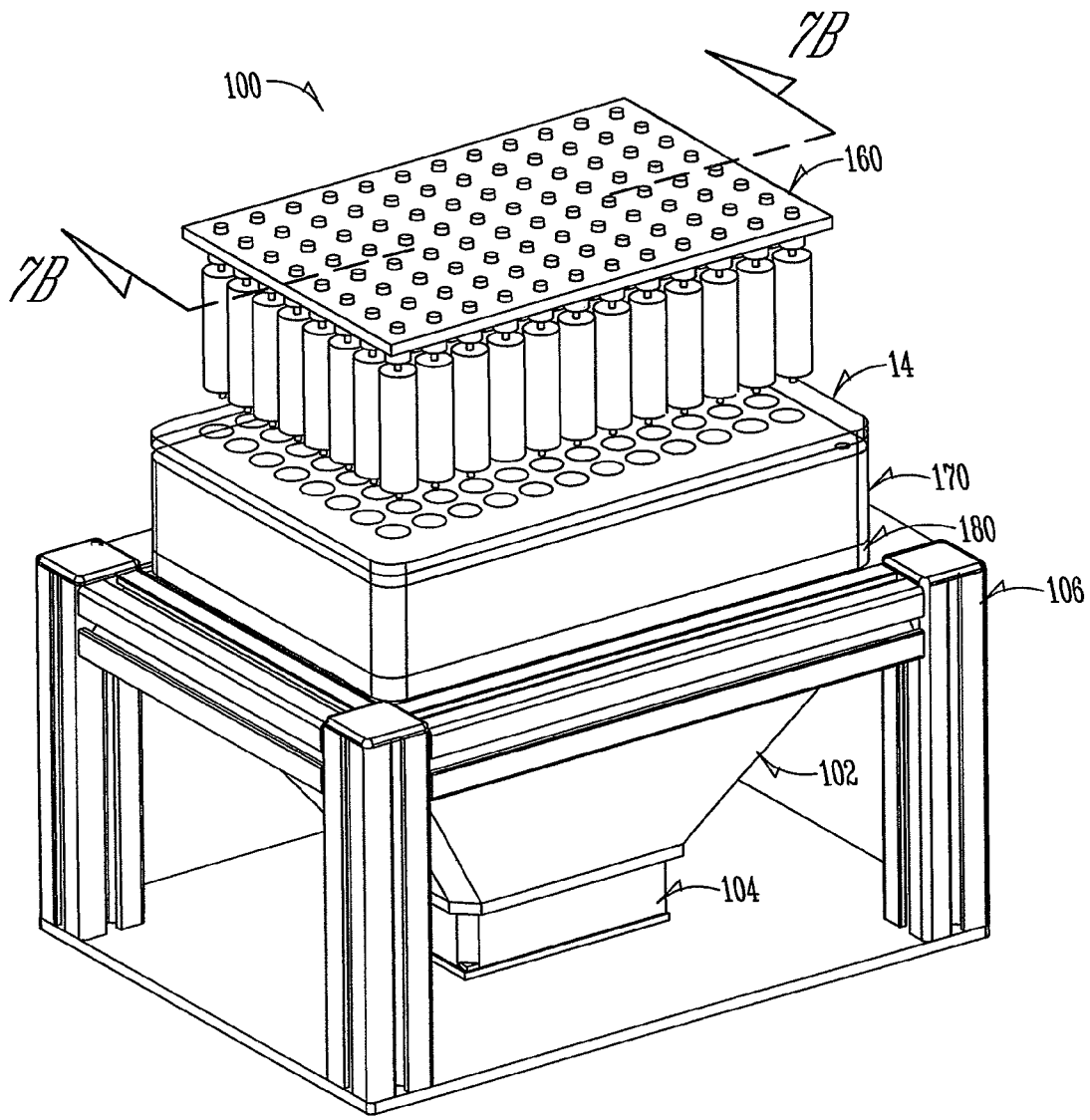
FIG. 7A is an isometric view of another exemplary embodiment of the present invention.
Figure 7B:
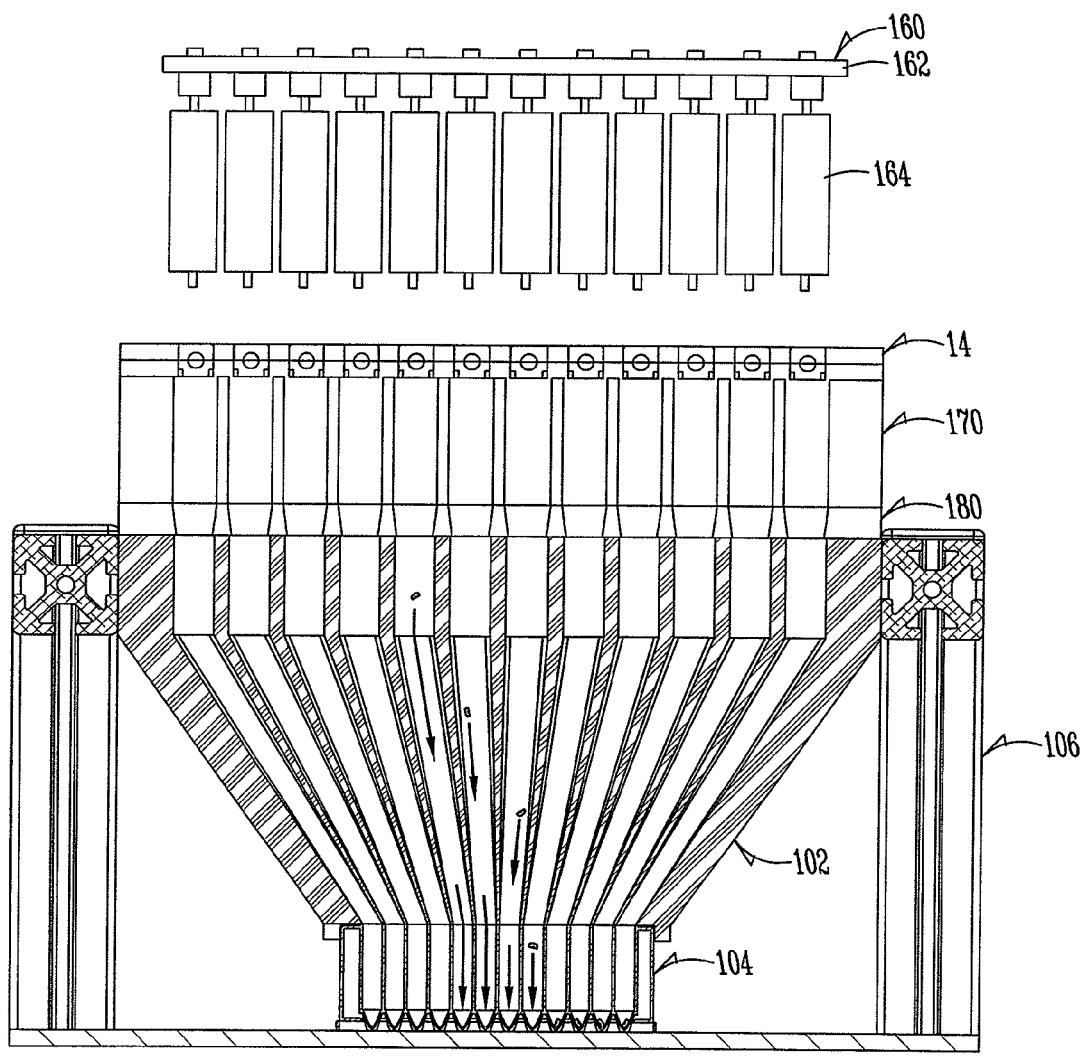
FIG. 7B is a cross-section view taken along line 7B-7B in FIG. 7A.
Figure 7C:
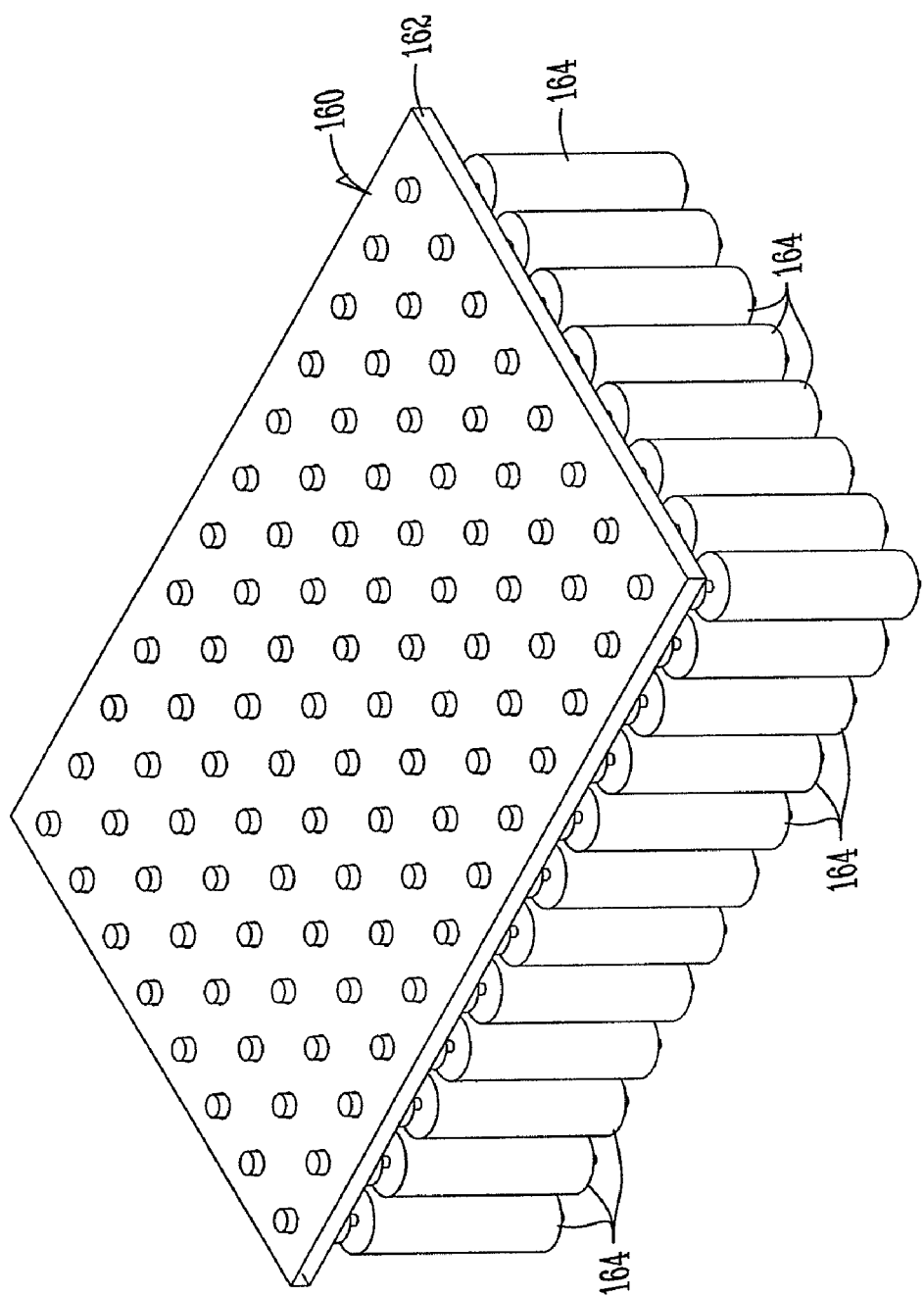
FIG. 7C is an isometric view of another example of a tool for displacing retained seed portions shown in FIG. 6A.
Figure 8B:
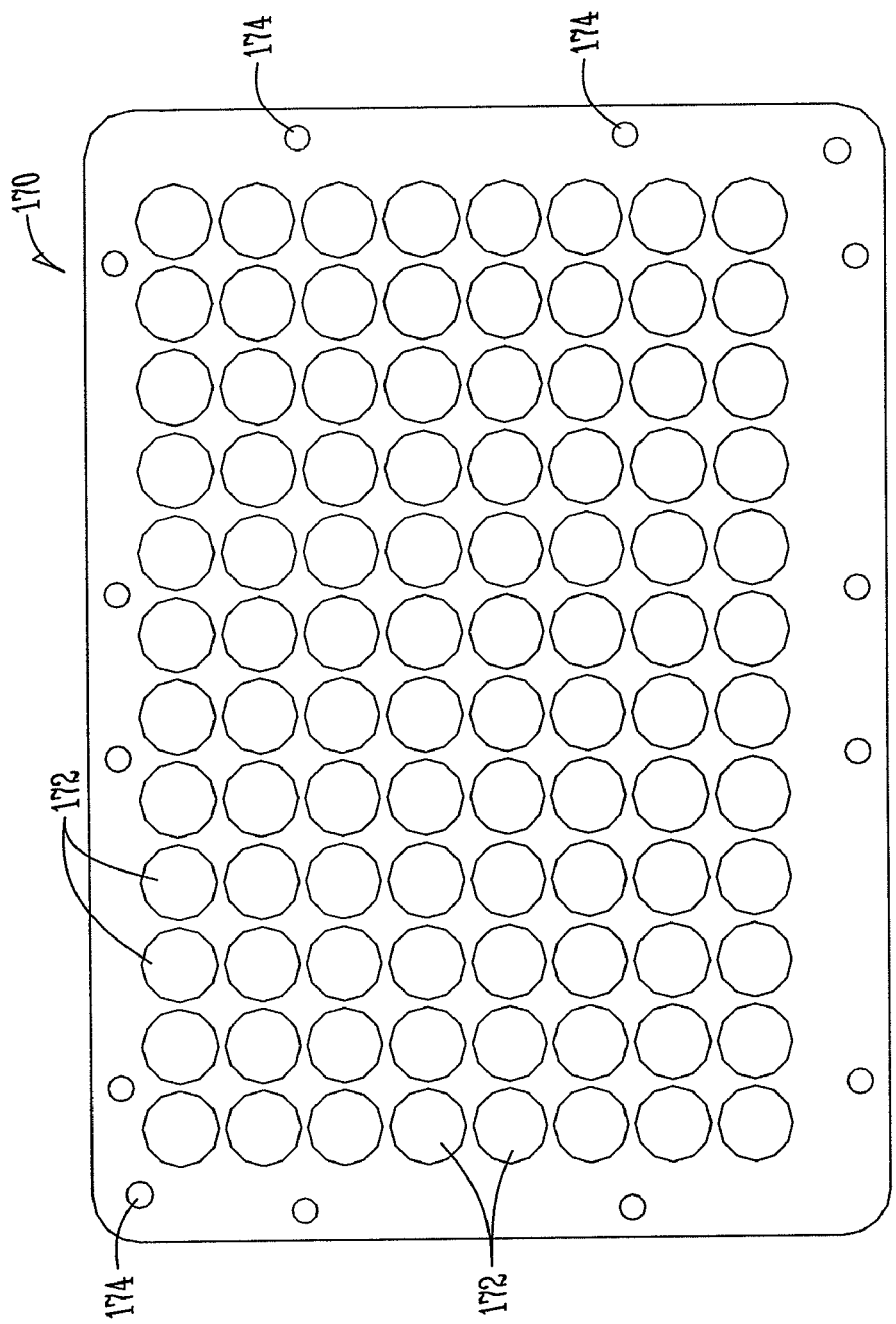
FIG. 8B is a plan view of the spacer plate shown in FIG. 8A.

FIGS. 6A-B and 7C-D show an exemplary embodiment of a tool to remove retained seed portions 32 from their respective carrying position 22 within carrier 14. Tool 152 shown in FIGS. 6A-B has a plate 154 with plural perpendicularly extending members 156. The plural perpendicularly extending members 156 are ganged on plate 154 having the same configuration as the plurality of apertures 20 in carrier 14. Tool 152 may have a handle for manual or automated operation. The diameter of the plural perpendicularly extending members 156 may be sized accordingly to fit within apertures 20 within the carrier 14 so that retained seed portions 32 are brushed off and released from their respective carrying position 22 within carrier 14. The plural perpendicularly extending members 156 may be formed of any material suitable for removing retained seed portions 32 and any residual matter that may have adhered to the carrier 14 during the seed ablation process. For example, the plural perpendicularly extending members 156 may be a brush made from an elastomer material, copper wire, or the like. Depending on the number of perpendicularly extending members 156 ganged on the plate member, the tool may be used to perform the aforementioned operation on some or all of the apertures 20 in carrier 14 at once. For example, FIGS. 7C-D shows a similar tool 160 with 96 perpendicularly extending members 164 ganged to plate 162. Tool 160 could be used to remove all retained seed portions 32 at once. To insure the retained seed portion 32 does not become trapped between one of the plural perpendicularly extending members 156, 164, and the sidewall of the carrier 14 or manifold 102, and spacer plate 170 and reducer plate 180, as shown in FIGS. 8A-9C, may be used in combination with manifold 102 as shown in FIG. 7C. In this aspect of the invention, carrier 14 is docked on top of spacer plate 170 using alignment/docking apertures 174. Spacer plate 170 is in-turn docked on top of reducer plate 180 using alignment/docking apertures 184. As best illustrated in FIGS. 7C and 8A-B, spacer plate 170 has conduits 172 having the same configuration as apertures 20 in carrier 14. The diameter of each conduit 172 in spacer plate 170 is larger than the diameter of the apertures 20 in carrier 14. The greater diameter of conduits 172 allows retained seed portions that may become trapped between a perpendicularly extending member 156, 164 and the sidewall of aperture 20 in carrier 14 to release and not be drawn back out of the carrier 14 when tool 152, 160 is removed. Reducer plate 180, as best illustrated in FIGS. 7C and 9A-C, has plural apertures 182 in identical configuration to conduits 172 in spacer plate 170. Each aperture 182 has tapered sidewalls 186, as best shown in FIG. 9C, to provide a seamless transition from the larger conduit 172 diameter of the spacer plate 170 to smaller conduit 108 diameter of manifold 102. The reducer plate 180 ensures that retained seed portions 32, removed from their respective carrying position 22 in carrier 14, do not get caught-up at some point in their downward transition between the space plate 170 and manifold 102.

Figure 15:
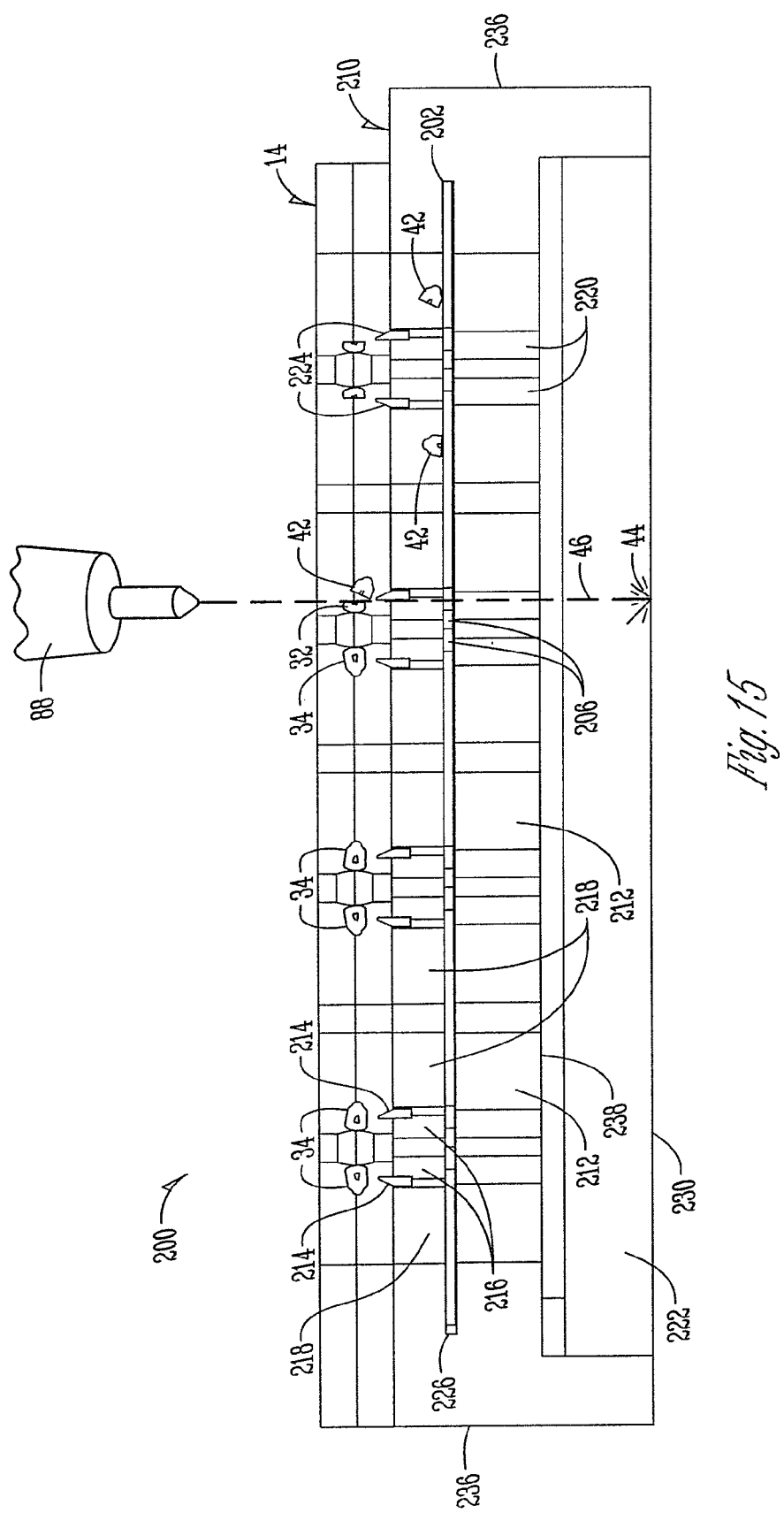
FIG. 15 is a section view taken along line 15-15 in FIG. 12.
Figure 16A:
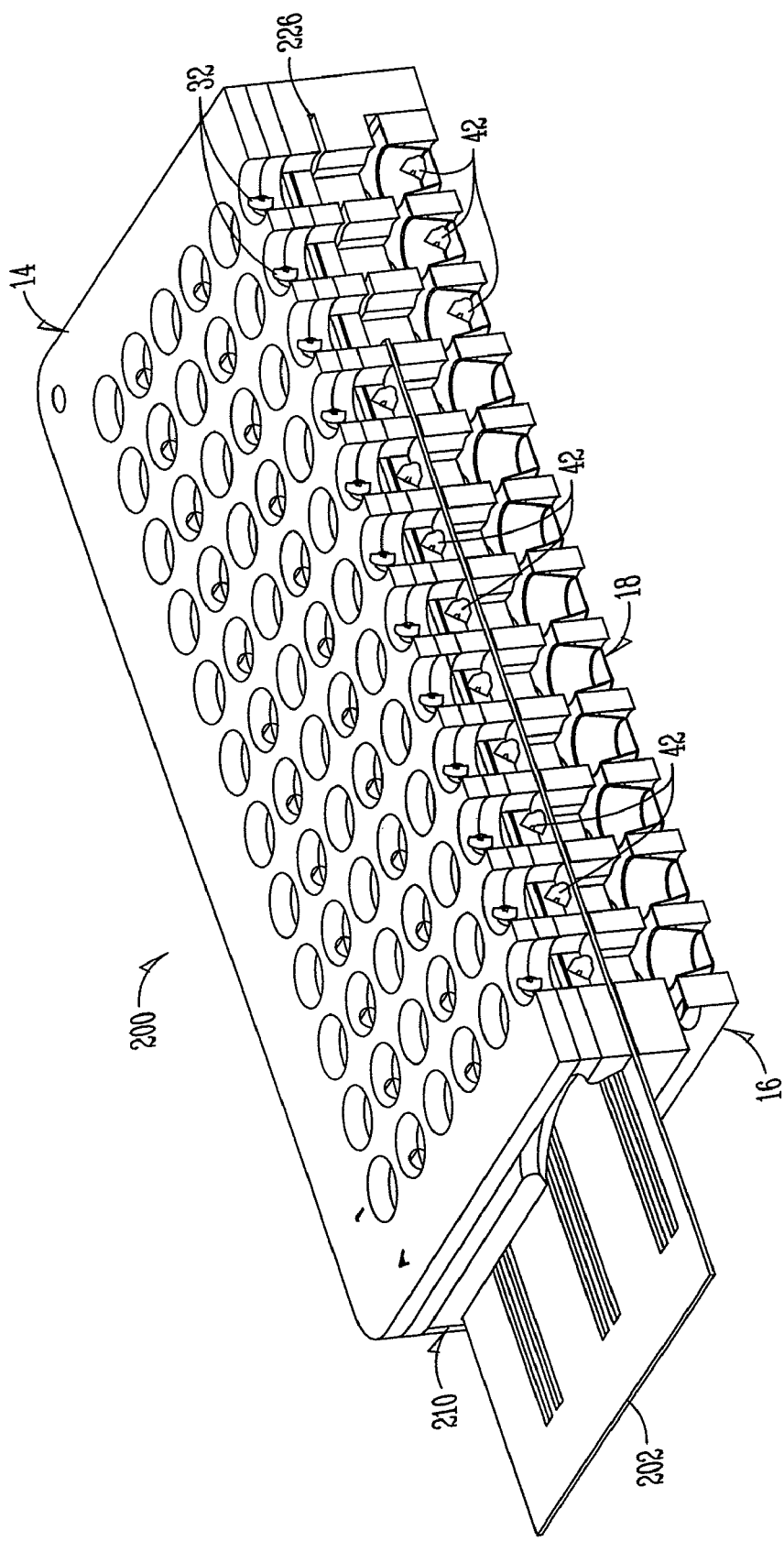
FIG. 16A is a section isometric view taken along line 16A-16A in FIG. 12.
Figure 16B:
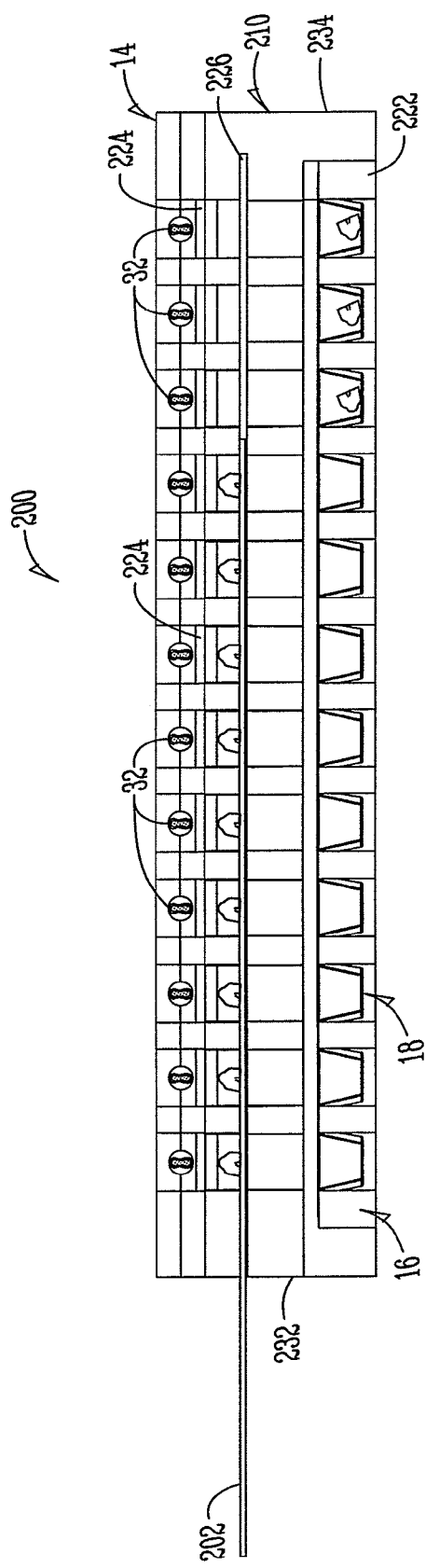
FIG. 16B is a section side elevation view taken along line 16B-16B in FIG. 12.

FIGS. 12-16B disclose another exemplary apparatus 200 of the present invention. Apparatus 200 includes the aforementioned carrier 14 which is dockable on the top surface 228 of manifold 210, as best illustrated in FIG. 12. Manifold 210 has a plurality of conduits 212 being configured in similar spaced relation to each other as apertures 20 in carrier 14. Conduits 212 extend through the entirety of manifold 210 and have the same diameter as apertures 20 in carrier 14, as is best illustrated in FIG. 15. Thus, when carrier 14 is docked on top of manifold 210, apertures 20 in carrier 14 are in communication with conduits 212 in manifold 210. Each row of conduits 212 in manifold 210 has a partition member 214. Partition member 214 is a thin planar strip that may have one contoured or beveled edge 224, as shown in FIG. 15. Partition member 214 is preferably positioned within a row of conduits 212 so that beveled edge 224 extends sufficiently above the top surface 228 of manifold 210 so that beveled edge 224 is positioned closely adjacent seed 34 in carrier 14, as best illustrated in FIG. 15. Partition member 214 is also preferably perpendicularly oriented relative the top surface 228 of manifold 210. One skilled in the art will appreciate that the beveled edge 224 and/or the partition member 214 may be positioned or oriented relative to the top surface 228 in a non-coplanar or non-perpendicular arrangement. Partition member 214 forms a first partition 216 and second partition 218 within each conduit 212 as shown in FIG. 13B. A slot 226 is configured longitudinally along an axis parallel to the top surface 228 within manifold 210. Outer edges of slot 226 run adjacent sidewalls 236 from the front 232 and terminate adjacent the back 234 of manifold as illustrated in FIGS. 15-16B. A shelf plate 202 having a sheet body 204 is configured to slide in and out of slot 226 in manifold 210. Shelf plate 202 has apertures 206. Apertures 206 are configured in shelf plate 202 so that when positioned within slot 226, apertures 206 are aligned with each first partition 216 of conduits 212 in manifold 210. Aligning apertures 206 in shelf plate 202 with each first partition 216 in manifold 210 provides a throughway 220 through conduit 212 when the shelf plate 202 is positioned within slot 226 as best illustrated in FIG. 15. Although shelf plate 202 leaves the first partition 216 of each conduit 212 open, the second partition 218 of each conduit 212 is occluded by shelf plate 202. When shelf plate 202 is removed from slot 226 in manifold 210, both first 216 and second 218 partitions within conduit 212 are open providing a throughway through manifold 210 from the top surface 228 through the body of the manifold 210 and out the bottom surface 238. FIG. 16A-B show how manifold 210 is fashioned with a slot 222 in the bottom surface 238 to accommodate the aforementioned and described jig 16 holding compartment layer 18. The jig 16 and compartment layer 18 may be slide in and out of slot 222 in manifold 210. The plurality of wells 142 in the compartment layer 18 are configured to match the plurality of conduits 212 within manifold 210 so that each conduit 212 at the bottom surface 238 opens into one of the wells 142 in compartment layer 18.

Method

FIG. 1 discloses one exemplary aspect of the method of the present invention using one or more of the previously described apparatuses for positioning and orienting seed for creating, partitioning, sorting, handling, collecting and indexing seed and viable seed portions or the like from plant seed. The method shown by the apparatuses in FIG. 1 teach in the broadest sense, in one aspect, positioning and orienting seed in a predetermined orientation using a carrier 14 for removing a seed portion from each seed in an efficient, non-lethal, non-contaminating and high throughput manner. In another aspect, handling, collecting and indexing the seed and seed portions (post-sampling) in an efficient, non-lethal, non-contaminating and high throughput manner.

In one exemplary method of the present invention, plant seeds 34 are coated with a magnetically responsive material 80 using an applicator 82, such as a spray can or gun, brush or the like. FIG. 1 illustrates one aspect of the present invention wherein kernels or plant seeds 34 are left intact on an ear of corn 84 and coated with magnetically responsive material 80. Corn seeds 34, while on the ear of corn 84, are all oriented in the same manner relative to the cob and each other with the crown portion of each seed 34 being exposed for application of magnetically responsive material 80. It should be appreciated that even though the present invention describes coating seeds 34 while still attached, seeds 34 could be coated with magnetically responsive material 80 after being removed. One example of a magnetically responsive material 80 suitable for coating the crown portion of seeds 34 is iron-based coatings such as an iron-based paint or the like. Commercially available materials such as MAGNAMAGIC'S ACTIVE wall magnetic paint or KRYLON'S magnetic spray paint could be used to coat seeds 34 in the manner previously described. Singulated seeds 34 with magnetically responsive material 80 are distributed within the plurality of apertures 20 in carrier 14. Seed orienter 24, such as a magnet positioned between sidewalls 26 of the pair of apertures 20, orients seeds 34 relative to each aperture 20 of the carrier 14 at carrying position 22. In a preferred form, a magnet is positioned in a similar location between each pair of apertures 20 in the carrier 14 so each seed 34 is oriented within carrier 14 in each row 28 in the same position relative to the carrying position 22 within aperture 20 of the carrier 14, as best illustrated in FIG. 3. Many of seeds 34 will automatically orient themselves relative to the carrying position 22 within each aperture 20 of the carrier 14 by virtue of the magnet or seed orienter 24. Carrier 14 may also be agitated up and down, back and forth, or otherwise to promote attachment and proper orientation of each seed 34 relative to the carrying position 22 within each aperture 20. In this manner, each aperture 20 of carrier 14 is loaded with a properly oriented, aligned and positioned seed 34.

In another aspect of the present invention, manifold 12 is docked within an ablation device 36. Ablation device 36 may be any device capable of ablating seed 34. For example, as previously discussed, ablation device 36 may be a laser engraver having a laser 88 emitting a laser beam 46 as shown in FIG. 3. In the case where the ablation device 36 is a laser, the present application contemplates that the laser could be a dual head laser, multi-head laser, galvo head laser, or any other suitable laser platform. As previously discussed, manifold 12 may have a bottom surface 72 having features suitable for docking manifold 12 within the ablation device 36. For example, bottom surface 72 of manifold 12 could have alignment pins, level adjustments and/or indicators to keep manifold 12 true and in the desired position within ablation device 36. With manifold 12 positioned within ablation device 36, as shown in FIG. 1, carrier 14 having seeds 34 within each aperture 20 may be docked with manifold 12, as shown in FIG. 3. Alignment pin 66 may be used to correctly dock carrier 14 with manifold 12 so that the plurality of apertures 20 in carrier 14 are aligned and in communication with the plurality of conduits 38 in manifold 12. The compartment layer 18, supported by jig 16, may be loaded into manifold 12 by inserting into the slot 58, as shown in FIG. 1. Jig 16 may have self-positioning and/or locating features, such as notch corner 52 to ensure that the plurality of compartments 48 within compartment layer 18 align and are in communication with the plurality of conduits 38 in manifold 12 when the compartment layer 18 and jig 16 are inserted within slot 58. With carrier 14 properly docked on manifold 12 and compartment layer 18 and jig 16 properly inserted within slot 58 of manifold 12, a throughway 86 is created as shown in FIG. 3 whereby viable seed portions 42 may be communicated from each carrying position 22 within aperture 20 of the carrier 14 through the plurality of conduits 38 into each compartment 48 of the compartment layer 18. With having the manifold 12, carrier 14, jig 16, and compartment layer 18 securely positioned within ablation device 36, the process of seed ablation may be started. For example, as previously discussed, the ablation device 36 may have an energy beam 46, such as a laser beam, that travels longitudinally across row 28 at a specified or programmed distance away from carrying position 22 so that seed 34 is ablated using energy beam 46. Alternatively, manifold 12 with carrier 12 could be moved relative to laser 88 having some fixed location in the ablation device 36. After ablation occurs, viable seed portions 42 fall from the carrying position 22 within each aperture 20 through the plurality of conduits 38 in manifold 12 coming to rest within the plurality of compartments 48 in compartment layer 18. Retained seed portion 32 is held at the carrying position 22 within each aperture 20 of carrier 14, as best illustrated in FIG. 3. Due to the contour of sidewalls 40 of conduit 38 in manifold 12, energy beam 46 is diffused as shown at 44 in FIG. 3, which prevents destruction, fatiguing or failure of compartment layer 18, as well as damage to seed or seed portions to maintain viability. By passing the ablation device 36 over the individual rows 28 and columns 30 of the carrier 14, viable seed portions 42 are created and communicated into each compartment 48 of the compartment layer 18 while retained seed portions 32 are kept at each carrying position 22 within aperture 20 of carrier 14. Each viable seed portion 42 is uniquely identifiable and/or positional addressable within each compartment 48 of compartment layer 18. Furthermore, each viable seed portion 42 within each compartment 48 of compartment layer 18 corresponds with and is traceable back to each aperture 20 within carrier 14. Filled with viable seed portions 42, compartment layer 18 and jig 16 may be removed from slot 58 in manifold 12. Furthermore, carrier 14 may be undocked from manifold 12 having retained seed portions 32 at each carrying position 22 within aperture 20 of carrier 14, as best illustrated in FIG. 1. Manifold 12 may be reloaded with another carrier 14 having seeds 34 properly positioned and oriented in each aperture 20 of the carrier 14. A new compartment layer 18 with a jig 16 may be inserted in slot 58 to perform the ablation process on a new set of seeds 34.

Having retained seed portions 32 in carrier 14, the carrier 14 is docked on manifold 102, as best illustrated in FIG. 6, to recover the retained seed portions 32 within each aperture 20. Similar to manifold 12, manifold 102 may have alignment pins 112 or other self-orienting and docking features adapted to correctly orient and dock carrier 14 with respect to manifold 102. A collector 104, as previously described, is docked within slot 120 of manifold 102. Preferably, collector 104 has self-orienting and positioning features, such as notch corner 138, so collector 104 may be properly oriented and positioned with respect to manifold 102. With carrier 14 properly docked on manifold 102 and collector 104 properly positioned under the bottom surface 124 of manifold 102, a throughway 150 is formed whereby retained seed portions 32 at carrying positions 22 within each aperture 20 of the carrier 14 may be passed into a plurality of compartments 128 within collector 104, as best illustrated in FIG. 7A. The present invention contemplates many ways for communicating retained seed portions 32 from carrying position 22 within each aperture 20 of the carrier 14 to the plurality of compartments 128 in collector 104. For example, in one aspect of the present invention, if magnets are used as the orienting feature or seed orienter 24, the magnets may be demagnetized or deactivated so as to release retained seed portions 32 whereby retained seed portions 32 fall from the carrying position 22 within aperture 20 through the plurality of conduits 108 in manifold 102 and into the plurality of compartments 128 within collector 104 to be collected within well 142 near the bottom surface 136 of collector 104. In another aspect of the present invention, as further illustrated in FIGS. 6A-B and 7A-C, a tool 152, 160 such as a brush, scraper, or prefabricated device having fingers suitable for inserting within apertures 20 of the carrier 14 may be used to scrape, remove, or displace retained seed portions 32 from carrying positions 22. For example, a plate member 154, 162 having one or more, or a gang of perpendicularly extending members 156, 164 such as a brush, sponge, elastomer member, or other seed displacing member, may be adapted to displace the retained seed portions 32 from carrying positions 22. In one embodiment, the tool 160 may include a plate member 162 configured with 96 perpendicularly extending members 164 to correspond with the pattern and number of apertures 20 in the carrier 14. In another aspect, the tool 152 may have a plate member 154 configured with a fewer number of perpendicularly extending members 156 to displace retained seed portions 32 from only a portion of the total number of apertures 20 at a time, such as would facilitate quick, efficient and accurate displacement of retained seed portions 32 from the carrying positions 22 in the carrier 14. In still another aspect, the plurality of conduits 108 in manifold 102 could be larger in diameter than the apertures 20 in carrier 14 to ensure that retained seed portions 32 are displaced into the plurality of conduits 108 and not bound-up or caught between the perpendicularly extending members 156 and the sidewalls 26, 126 of the plurality of apertures 20 or conduits 108. For example, carrier 14 could be docked on top of spacer plate 170 which is in-turn docked on top of reducer plate 180 which may in-turn be docked on top of manifold 102. Inserting perpendicularly extending members 156, 164 into apertures 20 in carrier 14 and conduits 108 in manifold 102 should release retained seed portions 32 from carrier 14. However, depending on size, retained seed portions 32 may get trapped between conduit 108 wall and perpendicularly extending members 164, 174. Thus, retained seed portions 32 may be drawn out of the carrier 14 with perpendicularly extending members 164, 174 when removed from within apertures 20 in carrier 14 and conduits 108 in manifold 102. To ensure retained seed portions 32 are released downward into conduits 108, a plate having conduits larger in diameter than apertures 20 in carrier 14, such as spacer plate 170, may be used in combination with a plate that transitions in diameter from the diameter of the larger conduits to the diameter of conduits 108 in manifold 102, such as reducer plate 180. In the preferred form, conduits 172 in spacer plate 170 would have a larger diameter than the perpendicularly extending members 156, 164 so that retained seed portions 32 would release from the perpendicularly extending members 156, 164 once moved into the larger diameter conduits 172 in spacer plate 170. After the retained seed portions 32 are released they would transition downward through conduits 172 and reducer plate 180 into conduits 108 in manifold 102. The tapered sidewall 186 allows retained seed portions 32 falling through conduit 172 in spacer plate 170 to transition smoothly from the larger diameter conduit 172 to the smaller diameter conduit 108 in manifold 102 thereby preventing seed from getting hung-up on their descent into collector 104. The present invention further contemplates semi-automatic and fully automatic operation, in addition to the possibility of manually operating tool 152, 160. One skilled in the art could appreciate the ease of which either tool 152, 160 could be configured to automatively move in and out of apertures 20 in carrier 14 to release retained seed portions 32 from carrier 14 to meet the high throughput objectives of the present invention. Thus far tools 152, 160 have been discussed in the context of seed removal, but tools 152, 160 would also serve to help clean and preserve a non-contaminated environment within apertures 20 in carrier 14 and conduits 108 in manifold 102, conduits 172 in spacer plate 170, apertures 182 in reducer plate 180, conduits 38 in manifold 12, and conduits 212 in manifold 210 for each set and subsequent set of seed and seed sample portions in keeping with another objective of the present invention to prevent contamination. The present invention contemplates, in addition to the aforementioned methods provided to displace retained seed portions 32, that forced air may be used to urge the retained seed portions 32 from the carrying position 22 within the aperture 20 through conduit 108 into compartment 128 of the collector 104. Seed portions 110 passing through the plurality of conduits 108 and manifold 102 are collected within the plurality of compartments 128 of the collector 104. Each seed portion 110 is uniquely identifiable and/or positionally addressable by row 130, column 132 or other indicia positioned on the top surface 134 of collector 104. Thus, seed portion 110 within well 142, located and positioned in row 1, column 1, may be correlated with or traced back to viable seed portion 42 collected in row 1, column 1 of compartment 48 in compartment layer 18. Collector 104 may be removed from the bottom side 124 of manifold 102 having seed portions 110 of the original seed 34 contained within each well 100 of the collector 104. Manifold 102 may be reloaded with another carrier 14 having retained seed portions 32 and a new collector 104 for collecting seed portions 110.

Figure 13A:
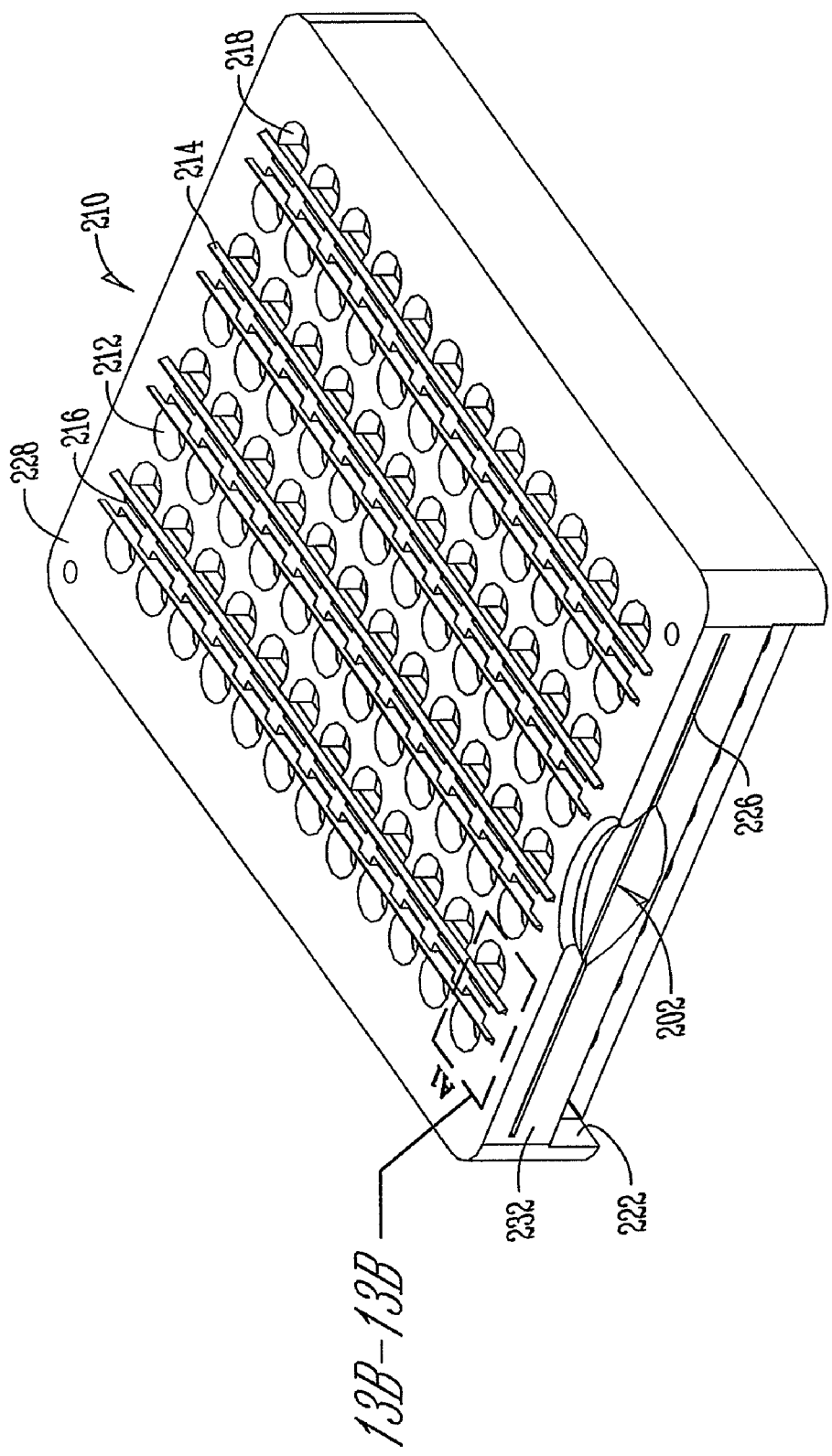
FIG. 13A is an isometric view of the manifold shown in FIG. 12.
Figure 13B:
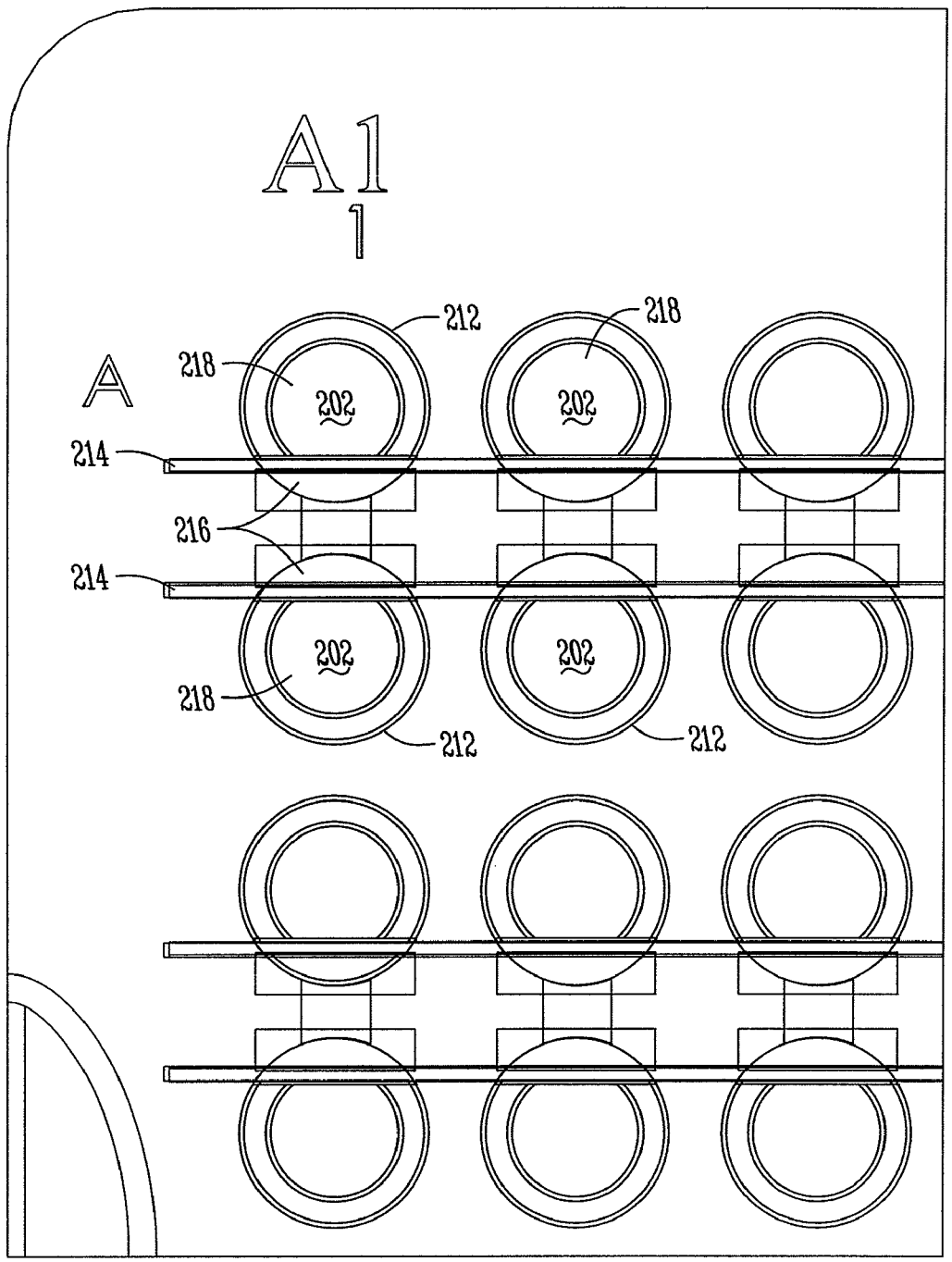
FIG. 13B is a section view taken along line 13B-13B in FIG. 13A.
Figure 14:
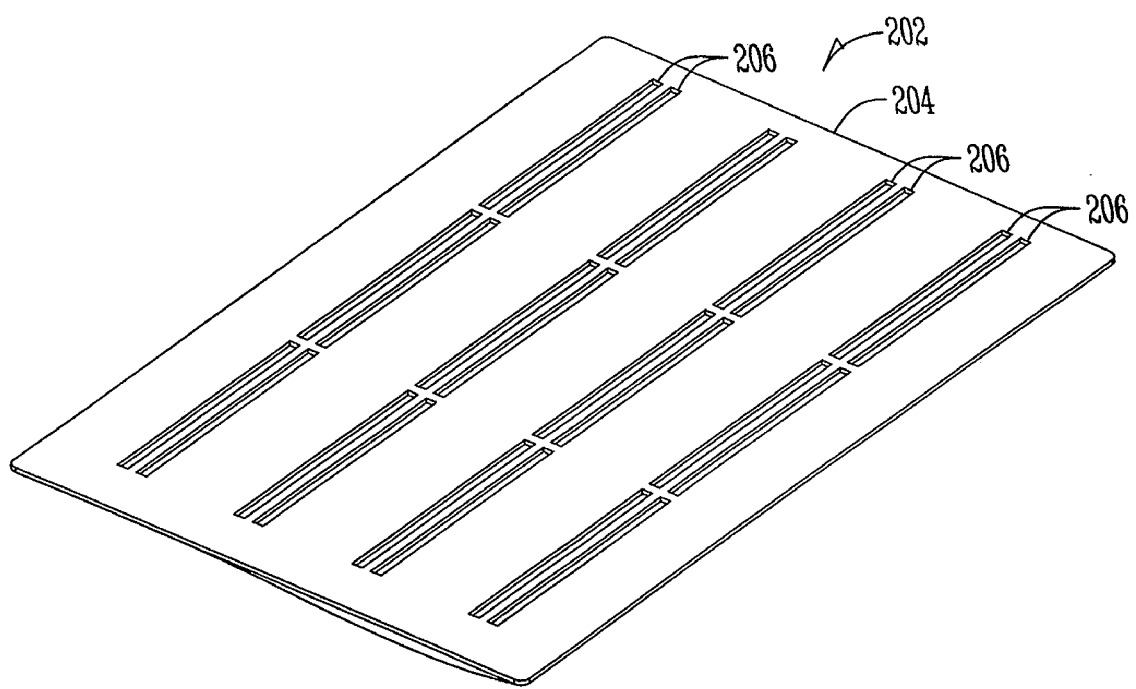
FIG. 14 is an isometric view of the shelf plate shown in FIG. 12.

In yet another aspect of the present invention, carrier 14 with seed 34 may be docked on the top surface 228 of manifold 210 having shelf plate 202 inserted within slot 226 as shown in FIG. 12. Manifold 210 (without jig 16 and compartment layer 18) may than be positioned within an ablation device 36, such as the laser engraver shown in FIG. 1, or any abating or sampling device suitable for ablating seed 34 in carrier 14 in an efficient and high throughput manner. For example, the ablation device 36 could use high energy streams of air, water, gas, particles or other matter to ablate seed 34 in carrier. The present invention is not limited in scope to use of high energy light (e.g., laser) to create seed portions from seed. Once manifold 210 is positioned within ablation device 36 the aforementioned process of ablating seed may be performed. The energy beam 46 from laser 88 ablates seed 34 in carrier, passes through the first partition 216 separated from the second partition 218 by partition member 214 (See FIG. 13B), exits from manifold 210 out the bottom surface 238, and is diffused upon impact of bed 230 of the ablation device 36 as best illustrated in FIG. 15. Once the seed 34 is ablated, seed portion 42 falls into second partition 218 coming to rest on shelf plate 202. The present invention appreciates that high throughput ablation techniques, although efficient, may pose a danger to seed 34, retained seed portions 32 and viable seed portion 42 if care is not taken to insure the high energy matter used to ablate seed 34 is diffused in a manner after ablation to prevent it from being reflected, deflected, or ricocheted back into contact with other unablated seed 34 (e.g., seed being ablated as well as other unablated seed in another aperture 20 of carrier 14), retained seed portions 32, or viable seed portion 42. Manifold 210 ensures seed 34, retained seed portion 32 and viable seed portion 42 are protected during the ablation process. This is accomplished by partition member 214 and shelf plate 202 (See FIG. 14) in manifold 210 as shown in FIG. 13A. Partition member's 214 beveled edge 224 positioned closely adjacent seed 34 in carrying position 22 in carrier 14, as best illustrated in FIG. 15. Energy beam 46 passes through seed medium and upon exiting seed medium passes immediately behind partition member 214 into first partition 216 of conduit 212. Viable seed portion 42, when detached from retained seed portion 32, falls into second partition 218 and comes to rest on shelf plate 202. Thus, any stray, reflected, deflected or ricocheted portions of energy beam 46 are kept from re-contacting and harming viable seed portion 32 by partition member 214 and shelf plate 202. Similarly, retained seed portions 32 are kept from harm by re-exposure to energy beam 46 because first partition 216 is relatively small and presents little or no opportunity for reflected or deflected energy from passing back through first partition 216 and coming into contact with retained seed portion 32. Having ablated seed 34 in carrier 14, retained seed portions are still at their respective carrying positions 22 in apertures 20 in carrier 14 and viable seed portions 42 are resting on shelf plate 202 within the second partition 218 of manifold 210. Carrier may be removed from off of manifold 210 and retained seed portions removed, collected and indexed according to the aforementioned details. Viable seed portions 42 are simply collected from manifold 210 by inserting jig 16 with compartment layer 18 into slot 222. Once jig 16 with compartment layer 18 is inserted into slot 222, and each conduit 212 in manifold 210 is in communication with a compartment 48 in compartment layer 18, shelf plate 202 is withdrawn from slot 226 out of manifold 210 as shown in FIGS. 16A-B. Viable seed portions 42 resting on shelf plate 202 are now permitted to continue in their descent through second partition 218 into compartment layer 18 for storing viable seed portions 42 in an indexed manner with respect to their retained seed portion 32 counterparts in collector 104. These same steps may be repeated by placing another carrier 14 with seed 34 on top of manifold 210, ablating seed 34, collecting viable seed portions 42 and retained seed portions 32, and indexing seed portions 42, 32 in respective containers 18, 104.

Once viable seed portions 42 and retained seed portions 32 have been properly indexed in compartment layer 18 and collector 104, compartment layer 18 and collector 104 can be taken to a location for further processing. In one example, retained seed portions 32 in collector 104 would each be individually analyzed to obtain biochemical, genetic, or phenotypic information of interest. In one example, this process could be used as a part of a plant advancement experiment where genetic or phenotypic traits of interest are to be identified to decide whether corresponding viable seed portions 42 has commercially valuable or desirable genetic or phenotypic traits. The viable seed portions 42 corresponding to the retained seed portions 32 can be easily and quickly identified by its corresponding index position in compartment layer 18 and can be shipped to an experimental growing location where it can be planted. As previously mentioned, the apparatuses, methods and systems of the present invention are designed to have a substantially high probability that viable seed portions 42 will germinate at the growing location.

One type of biochemical analysis could include a protein assay which requires protein extraction from the retained seed portions 32. One example of protein extraction is P-PER® Plant Protein Extraction Kit (Pierce Biotechnology). Other examples involve common grinding aids such as a mortar and pestle, Biomasher (Cartagen), or polypropylene pestle (Kontes) and a suitable extraction buffer. Other types of biochemical analysis could include oil or starch analysis. Still further types of biochemical analysis are possible and are well-known in the art.

One type of genetic analysis for the retained seed portions 32 is DNA extraction. One example of DNA extraction is standard Extract N Amp (Sigma-Aldrich) protocol (other examples include, e.g., standard CTAB protocol and HotShot methods). Other types of genetic analysis, such as, but not limited to, RNA analysis, are also possible and are well-known in the art. Some analyses will include phenotype-based data in which specific seed morphologies are analyzed. A phenotype based analysis may be accomplished spectroscopically under a variety of light wavelengths. Alternatively it could be done manually by observation. In this scenario, the use of magnetically oriented seed allows the researcher to consistently hold an individual seed with specific reference to morphologies of interest. In this scenario the seed may be sampled or left unsampled so the spectroscopic or manual observations may occur. Specific observations may include, but would not be limited to, seed color, opacity, starch content, oil content and seed shape. As well known in the art, a variety of other observations are possible.

Bar codes could be used and created for each compartment layer 18 and collector 104 so that information about the contents of each can be recorded and stored and easily retrieved by scanning the bar codes. Commercially available equipment can be used for these functions and programmed to meet the needs of the application.

System

FIG. 1 discloses one exemplary aspect of the system of the present invention using one or more of the previously described apparatuses or methods for positioning and orienting seed for creating, partitioning, sorting, handling, collecting and indexing seed and viable seed portions or the like from plant seed. The system shown by the apparatuses and methods of FIG. 1 teach in the broadest sense, in one aspect, a system having a carrier or similar construct for positioning and orienting seed in a predetermined orientation. In another aspect, the system may also include an ablation device for removing a seed portion from each seed in the carrier an efficient, non-lethal, non-contaminating and high throughput manner. In still another aspect, the system may also include one or more manifolds for handling sampled seed and seed portions post-ablation. In yet another aspect, the system may also include a compartment layer and another collector for collecting and indexing the seed and seed portions in both to each other in an efficient, non-lethal, non-contaminating and high throughput manner.

The exemplary embodiments of the present invention, in methods and apparatuses, have been set forth in the drawings and specification, and although specific terms are employed, these are used in the generically descriptive sense only and are not used for the purposes of limitation. Changes in the formed proportions of parts, as well as in substitutions of equivalents are contemplated as circumstances may suggest or rendered expedient without department from the spirit and scope of the invention as further defined in the following claims.

Any references in the Specification are herein incorporated by reference in their entirety.

What is claimed is:

1. A method for creating, handling and collecting seed portions comprising:
   taking a carrier having one or more carrying positions;
   positioning and orienting a seed relative to the carrying position in the carrier;
   ablating the seed with a seed ablation device; and
   communicating seed sample and sampled seed through manifolds into collectors.

2. The method of claim 1 further comprising the step of coating a crown portion of the seed with a magnetically active material for orienting the seed relative to the carrying positions in the carrier with a magnet.

3. The method of claim 1 further comprising the step of docking the carrier on top of the manifold and positioning the collector within the manifold.

4. The method of claim 1 further comprising the step of
   a. removing collector with sampled seed from the manifold;
   b. retaining seed samples at the carrying positions;
   c. removing the carrier with seed samples from off of the manifold; and
   d. docking the carrier with a second manifold adapted to communicate seed samples at the carrying positions into a collector by releasing seed samples from the carrying positions in the carrier.

5. A method for creating, handling and collecting seed portions comprising:
   coating a crown portion of a seed with a magnetically responsive material;
   taking a carrier having one or more carrying positions;
   positioning and orienting the crown portion of the seed relative to the carrying position in the carrier with a magnet;
   ablating the seed with the seed ablation device to create a seed portion;
   communicating the seed portions through a plurality of conduits in a manifold into a plurality of compartments in a compartment layer; and
   retaining the other seed portions at the carrying positions in the carrier for collection in a collector.

6. The method of claim 5 further comprising the step of
   a. docking the carrier on top of the manifold whereby the carrying positions in carrier mate with the plurality of conduits in the manifold; and
   b. positioning the compartment layer within the manifold.

7. The method of claim 5 further comprising the step of removing the carrier having the plurality of retained seed portions from the manifold for docking the carrier with a second manifold adapted to communicate the plurality of retained seed portions from the carrying positions in the carrier into a plurality of compartments in the collector by releasing the plurality of retained seed portions from the carrying positions in the carrier.

8. A method for handling seed and seed portions removed from the seed in an efficient and high throughput manner, the method comprising:
providing a seed manifold having a plurality of conduits there-through, a partition member dividing a portion of each conduit into first and second partitions, and a slot for accommodating a plate;
docking a seed carrier on top of the seed manifold, the carrier having seed pre-positioned and pre-oriented within apertures in the seed carrier;
ablating the seed with a seed ablation device to create the seed portion;
passing energy exiting the seed through the first partition out the bottom of the seed manifold; and
capturing the seed portion in the second partition to prevent inadvertent exposure to direct or reflected energy from the seed ablation device.

9. The method of claim 8 further comprising the step of aligning a plurality of apertures in the plate with the second partition in the seed manifold for creating a throughway for energy from the ablation device to pass there-through.

10. The method of claim 9 further comprising the step of inserting a compartment layer underneath the seed manifold to align a plurality of compartments in the layer with the plurality of conduits in the seed manifold.

11. The method of claim 10 further comprising the step of:
a. sliding the plate into the slot in the seed manifold to close-off a portion of the second partition to capture the seed portion ablated from the seed and prevent inadvertent contact with energy from the ablation device; and
b. sliding the plate out of the slot in the seed manifold to release seed portions within the second partitions into the plurality of compartments to collect the seed portions in the compartment layer.

12. The method of claim 11 further comprising the step of removing the seed carrier with retained seed portions from the seed manifold for docking onto another manifold having a plurality of conduits for communicating seed portions removed from the carrier into a collector.

13. The method of claim 8 further comprising the step of indexing the position of the sampled seed and respective seed portions in the compartment layer and collector.

14. A system for creating, handling, collecting and indexing seed and seed portions removed from the seed in an efficient and high-throughput manner, the system comprising:
a seed ablation device adapted to sample a seed by removing a seed portion from the seed; and
a seed manifold having a plurality of conduits adapted to communicate the sampled seed into one collector and seed portions into another collector.

15. The system of claim 14 further comprising a seed carrier having a plurality of apertures adapted to position and orient seed relative to the carrier, the seed carrier adapted to dock on top of the seed manifold.

16. The system of claim 14 further comprising another seed manifold having a plurality of conduits adapted to communicate seed portions retained with the seed carrier into the collector having compartments indexed to correlate with the seed carrier and other collector.

17. The system of claim 14 wherein the seed manifold further comprises:
a. a partition member adapted to partition each of the plurality of conduits into first and second partitions; and
b. a slot extending longitudinally there-through, the slot adapted to receive a plate with apertures, wherein a portion of the second partition closed-off by the plate is adapted to capture and separate the seed portion to prevent inadvertent contact with energy from the ablation device.

18. The system of claim 17 wherein the apertures in the plate align with the first partition in the seed manifold to provide a throughway to pass energy from the seed ablation device through to be diffused or absorbed outside of the seed manifold to prevent reflected energy from damaging the seed or seed portion.

19. The system of claim 18 wherein the partition member has a vertical most edge, the vertical most edge being closely adjacent the underside of the seed in the seed carrier whereby energy from the ablation device exiting the seed passes immediately into the first partition formed by the partition member to prevent inadvertent contact of the seed or seed portion with reflected energy.

20. The system of claim 14 wherein the seed manifold is adapted to receive a collector, wherein the seed portions in the second partition are moved into the collector by removing the plate from the slot in the seed manifold.

* * * * *